United States Patent
Konno

(10) Patent No.: US 7,391,845 B2
(45) Date of Patent: Jun. 24, 2008

(54) SEMICONDUCTOR RADIATION DETECTOR WITH GUARD RING, AND IMAGING SYSTEM WITH THIS DETECTOR

(75) Inventor: Yasutaka Konno, Saitama (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 11/798,753

(22) Filed: May 16, 2007

(65) Prior Publication Data

US 2007/0280409 A1    Dec. 6, 2007

(30) Foreign Application Priority Data

May 30, 2006    (JP)    .............................. 2006-149524

(51) Int. Cl.
*H05G 1/64*    (2006.01)

(52) U.S. Cl. ...................... 378/19; 378/98.8; 250/208.1; 250/370.09

(58) Field of Classification Search .................... 378/19, 378/98.8; 250/208.1, 370.08, 370.09, 370.11
See application file for complete search history.

(56) References Cited

U.S. PATENT DOCUMENTS 6,396,898 B1    5/2002    Saito et al. ..................... 378/19
6,696,817 B2    2/2004    Awatsu et al. ................ 320/112
6,928,144 B2    8/2005    Li et al. ....................... 378/98.8

FOREIGN PATENT DOCUMENTS

| JP | 61-289677 | 6/1985 |
| JP | 07-333348 | 6/1994 |
| JP | 2000-316841 | 5/1999 |
| JP | 2001-242253 | 11/2000 |
| JP | 2003-7275 | 2/2002 |
| JP | 2004-024659 | 6/2002 |
| JP | 2005-159156 | 11/2003 |
| JP | 2005-57281 | 7/2004 |

*Primary Examiner*—Courtney Thomas
(74) *Attorney, Agent, or Firm*—Reed Smith LLP; Stanley P. Fisher, Esq.; Juan Carlos A. Marquez, Esq.

(57) ABSTRACT

A guard-ring electrode can be used at a suitable position for each of a plurality of imaging regions. Improvement in image quality and reduction in unnecessary radiation exposure, such as reduction in artifacts or noise, improvement in SNR, and expansion in dynamic range, are realized by reducing the cross-talk or the inflow of electrical charges from ineffective regions. Based on a radiation detector having a plurality of pixel electrodes 117 and a common electrode that sandwich a photoelectric conversion layer, an interelement guard-ring electrode 111 is adjacently disposed between the pixel electrodes 117 of the radiation detecting element, and the interelement guard-ring electrode 111 is switched between an electrically open-circuit state and a ground-potential connection state, so as to change the area in which the radiation detecting element detects radiation.

20 Claims, 20 Drawing Sheets

SEMICONDUCTOR RADIATION DETECTOR WITH GUARD RING, AND IMAGING SYSTEM WITH THIS DETECTOR

CLAIM OF PRIORITY

The present application claims priority from Japanese application JP 2006-149524 filed on May 30, 2006, the content of which is hereby incorporated by reference into this application.

BACKGROUND OF THE INVENTION

1. Field of the Invention

The present invention relates to radiation/X-ray imaging systems, such as medical X-ray/radiation imaging systems, X-ray inspection systems, X-ray analysis systems, and radiation monitoring systems, and to semiconductor radiation detectors used in these systems.

2. Background Art

Cases in which an X-ray detector, which is one example of a semiconductor radiation detector, is applied to a multi-slice X-ray CT scanner will be hereafter described as a representative example. An X-ray CT scanner is an apparatus with which imaging is conducted on an object in a plurality of directions, and it calculates X-ray attenuation coefficients based on the projection, so as to obtain cross-sectional views of the object. Such X-ray CT scanner is widely used in the field of medicine or nondestructive testing. Patent Document 1 is a typical example thereof. In order to realize such imaging, for example, an X-ray tube and an X-ray detector are disposed so that they sandwich the object, and they are mounted on a rotated gantry so that they can move around the object. This X-ray detector is composed of a plurality of X-ray detecting elements that are disposed approximately in an arc having the X-ray tube as its center. A system (indirect type) in which an X ray is detected by a scintillator so as to covert it into light, and the light is then converted into an electric signal by a silicon wafer or the like is mainly used for the X-ray detecting elements.

Further, regarding the multi-slice X-ray CT scanner, a plurality of stages of X-ray detecting element rows are also formed in the direction of the axis of rotation (in the direction of slice). Use of such X-ray detector in which the X-ray detecting elements are disposed in a two dimensional manner enables imaging with a wide field of view in the direction of the axis of rotation in one imaging or enables imaging with a wide field of view in a short amount of time, and therefore, the multi-slice X-ray CT scanners are increasingly widespread.

As shown in Patent Document 2, regarding the X-ray detectors used for the multi-slice X-ray CT scanners, a system in which the X-ray detecting elements are provided with readout circuits on a one-on-one basis has been conventionally used. However, because the number of circuits is increased as the multi-slice type is increasingly widespread as described above, as a structure that can prevent such increase, X-ray CT scanners equipped with X-ray detectors of a sequential readout system as indicated in Patent Document 3 have also been proposed. In this system, a capacitor for accumulating electric signals for each of the X-ray detecting elements and a switch for outputting the electron signals are provided, and the X-ray detecting elements in the same column (channel) are connected to the same readout circuit. With this structure, by turning on the switch, signals from the X-ray detecting elements in one row (slice) are obtained, and by sequentially changing the row, the elements to be read are switched, whereby signals from the X-ray detecting elements in different rows can be obtained from a common readout circuit. Thus, such structure in which a readout circuit is commonly used provides the advantageous effect of reading signals with a fewer readout circuits, as compared with conventional systems.

Meanwhile, based on multi-slice, since a sufficiently wide field of view can be realized even with pixel elements having a small size in the slice direction, the size of pixel elements in the slice direction is increasingly reduced. For example, while the size of a pixel element in the slice direction was on the order of 10 mm in the case of a single slice, it is on the order of 1 mm in the case of 16 slices or the like. For example, as described in Patent Document 4, in a reconstructed image, spatial resolution equal both in the slice direction and the channel direction is about to be realized. However, since signals generated from one pixel element are reduced along with such decrease in the size of pixel elements, the SNR is decreased and image quality is decreased due to the influence of circuit noise particularly at the time of low dose. As a method for preventing this, a direct-type detector that directly converts X rays into electric signals is applied. Based on this detector, by using amorphous selenium (a-Se), cadmium telluride (CdTe), cadmium zinc telluride (CdZnTe), mercuric iodide ($HgI_2$), or the like as a photoelectric conversion material that converts X rays into electric signals, it becomes possible to generate more electric signals per X-ray photon than an indirect-type detector. For example, Patent Document 5 is a typical example of this direct-type X-ray CT scanner.

In these X-ray detectors, generally, many X-ray detecting elements are formed on a semiconductor module or a module comprising a semiconductor layer. Based on such structure, since the X-ray detecting elements are adjacent to one another, separation between the elements is insufficient. Thus, due to voltage nonuniformity in the semiconductor module or the semiconductor layer, electrical charge drift, or the like, there are cases in which the inflow of signals from adjacent pixel elements or peripheral pixel elements is caused. This is referred to as "cross-talk." Particularly, in the case of the direct type, since a relatively thick semiconductor module or semiconductor layer is necessary for detecting X rays, such cross-talk is easily caused. As a method for preventing this, Patent Document 2 proposes a structure in which a groove is provided between X-ray detecting elements so as to realize the separation (guard-ring) of X-ray detecting elements. Patent Document 6 proposes a structure for substantially realizing guard-ring in order to obtain a similar effect; that is, the periphery of the electrodes of X-ray detecting elements is provided with a guard-ring electrode, instead of a groove, and a voltage is made uniform thereby in the semiconductor module or the semiconductor layer. In this way, even when electrical charge drift is caused, before flowing into other pixel elements, it is read by the guard-ring electrode guard-ring. Further, Patent Document 7 proposes a structure to remove or reduce the distortion of the electric fields in the X-ray detecting elements located at the end portions and prevent the inflow of signals from ineffective regions by providing a guard-ring electrode so that it surrounds the entire X-ray detecting region. Based on these guard-ring structures, the cross-talk or leak currents from ineffective regions can be reduced.

Patent Document 1: JP Patent Publication (Kokai) No. 2001-242253 A

Patent Document 2: JP Patent Publication (Kokai) No. 2000-316841 A

Patent Document 3: JP Patent Publication (Kokai) No. 2003-7275 A

Patent Document 4: JP Patent Publication (Kokai) No. 2004-24659 A

Patent Document 5: JP Patent Publication (Kokai) No. 7-333348 A (1995)

Patent Document 6: JP Patent Publication (Kokai) No. 2005-159156 A

Patent Document 7: JP Patent Publication (Kokai) No. 2005-57281 A

SUMMARY OF THE INVENTION

When the X-ray CT scanner is used, as disclosed in Patent Document 2, there are cases in which imaging is conducted by changing the slice thickness with which reconstruction is conducted or the slice width with which imaging with X-ray irradiation is conducted. Regarding such change in slice thickness, there is a reconstruction method in which signals from X-ray detecting elements adjacent in the slice direction are subjected to weighted summation (to be hereafter referred to as "binning") depending on imaging conditions, and the signals are virtually considered to be a signal from one element. There are cases in which such addition is conducted on analog signals and cases in which it is conducted on digital signals. Such processing is advantageous in that reconstructed images having less noise can be obtained, the volume of data can be compressed, and transfer/processing time can be reduced, for example.

When this binning is not conducted, it is desirable that the above guard-ring structure be provided between X-ray detecting elements so as to reduce the cross-talk or leak currents from ineffective regions. However, when the binning is conducted, in order to reduce unnecessary radiation exposure or increase the SNR of obtained signals, it is desirable that the signals of X rays incident between X-ray detecting elements be also used for forming images. However, when there is a guard-ring structure, such as a guard-ring electrode or a groove between the X-ray detecting elements, it is problematic in that signals incident between the X-ray detecting elements cannot be obtained.

When the slice width with which imaging is conducted is changed, in the case of a 16-slice detector, for example, a selection is made so that the central two slices, four slices, or eight slices are used, and a detector region in which signals are read and an X-ray irradiation region are individually changed. In such case, as disclosed in Patent Document 7, it is desirable that a guard-ring electrode be provided so that it surrounds the entire X-ray detecting region so as to remove or reduce the distortion of electric fields of the X-ray detecting elements located at the end portions. However, based on conventional technology, it is difficult to realize such guard-ring at the end portions of each X-ray detecting region.

In one method, the empty reading of the X-ray detecting elements disposed in the regions (ineffective regions) outside the region in which readout is conducted by detecting X rays is conducted and a certain voltage is applied thereto. By making an electrical potential in the semiconductor module or the semiconductor layer uniform, the electrodes of these X-ray detecting elements can be used as guard-ring electrodes. However, in the case of an X-ray detector of a sequential readout system, since a common readout circuit is connected, in order to apply a voltage to the X-ray detecting elements in ineffective regions, switches need to be turned on, and thus signals from the X-ray detecting elements in the X-ray detecting region cannot be separately read. Thus, the X-ray detecting elements in the ineffective regions cannot be used as guard-ring electrodes. Thus, in the case of a detector of a sequential readout system, when the slice width with which imaging is conducted is changed, it is problematic in that the electrodes of the X-ray detecting elements in the ineffective regions cannot be used as guard-ring electrodes.

It is an object to the present invention to make it possible to use guard-ring electrodes at locations suitable for each of a plurality of imaging regions, reduce the cross-talk or the inflow of electrical charges from ineffective regions, reduce artifacts or noise, and expand the dynamic range. Further, another object is to reduce unnecessary radiation exposure, increase the amount of signal obtained, and improve the SNR of an image, by making it possible to read radiation signals incident on the guard-ring electrode location at the time of binning.

A radiation detector according to the present invention comprises a photoelectric conversion layer, a plurality of pixel electrodes with which the photoelectric conversion layer is provided, a common electrode with which the photoelectric conversion layer is provided so that the common electrode is opposite to the plurality of pixel electrodes, a guard-ring electrode disposed between adjacent pixel electrodes that comprise at least part of the plurality of pixel electrodes, and a controller for switching a terminal connected to the guard-ring electrode between an electrically open-circuit state and an ground-potential connection state. The controller controls the area of a radiation detecting region based on the switching between the electrically open-circuit state and the ground-potential connection state. When the controller switches the terminal connected to the guard-ring electrode so that the terminal is connected to ground potential, it becomes possible to reduce noise and expand the dynamic range due to reduction in cross-talk and leak currents from ineffective regions. On the other hand, when the terminal connected to the guard-ring electrode is caused to be in the electrically open-circuit state, it becomes possible to increase the SNR due to reduction in unnecessary radiation exposure or increase in the amount of signal obtained. By realizing these in accordance with imaging conditions, a radiation detector having higher image quality and fewer artifacts can be obtained.

In cases in which one region of a plurality of pixel electrodes is used as a radiation detecting region and the controller controls the guard-ring electrode that is located outside the radiation detecting region and that is adjacent to pixel electrodes in the radiation detecting region so that the guard-ring electrode is connected to ground potential, even when the radiation detecting field of view is changed, it becomes possible to provide the end portions of the radiation detecting region with the guard-ring electrode, reduce noise and expand the dynamic range due to reduction in cross-talk and leak currents from ineffective regions.

In another embodiment, the present invention comprises a binning means that conducts binning on adjacent pixel electrodes that sandwich the guard-ring electrode. When the binning means conducts binning and when the terminal of the guard-ring electrode sandwiched between the pixel electrodes on which binning is conducted is caused to be in the electrically open-circuit, signals generated due to radiation incident between the pixel electrodes on which the binning is conducted can be obtained when reading these pixel electrodes. Further, it is possible to reduce unnecessary radiation exposure and increase the amount of signal obtained when the binning is conducted.

Further, when the present invention is applied to a radiation detector of a sequential readout system, the guard-ring electrode located immediately outside the radiation detecting region of the pixel electrodes in accordance with on the imaging field of view (FOV) depending on imaging conditions is connected to ground potential, so as to realize the guard-ring function. In such case, since the guard-ring is realized, due to the elements detecting radiation, it is possible to reduce noise and expand the dynamic range due to reduction in cross-talk or leak currents from ineffective regions.

An X-ray imaging system equipped with the radiation detector of the present invention can also provide the same effects. Namely, since the location of the guard ring or the presence/absence of the guard-ring can be changed in accordance with the imaging region having a different radiation detecting region or with the binning size of radiation detecting elements, an X-ray image having higher image quality and fewer artifacts can be obtained. Further, since an X-ray CT scanner equipped with the radiation detector of the present invention can change the location of the guard ring or the presence/absence of the guard ring in accordance with the slice thickness with which reconstruction is conducted or with the slice width with which imaging is conducted, a reconstructed image with higher image quality and fewer artifacts can be obtained.

In accordance with the present invention, it is possible to provide a semiconductor radiation detector and a radiation/X-ray imaging system equipped therewith that can realize improvement in image quality and reduction in unnecessary radiation exposure in accordance with the imaging FOV or binning conditions, while suppressing the cross-talk, the occurrence of artifacts due to leak currents from the ineffective regions, the reduction in quantitative characteristics, the reduction in spatial resolution or time resolution, the increase in noise, and reduction in dynamic range.

DESCRIPTION OF PREFERRED EMBODIMENTS OF THE INVENTION

Embodiments of the present invention will be described hereafter with reference to drawings.

Embodiment 1

The present embodiment relates to a medical X-ray CT scanner, which is an object to which the present invention is applied, and in the present embodiment, the position or the presence/absence of a guard-ring can be changed in accordance with conditions of the imaging field of view (FOV). Embodiment 1 of the present invention will be described hereafter with reference to FIGS. 1 to 11.

Figure 1:
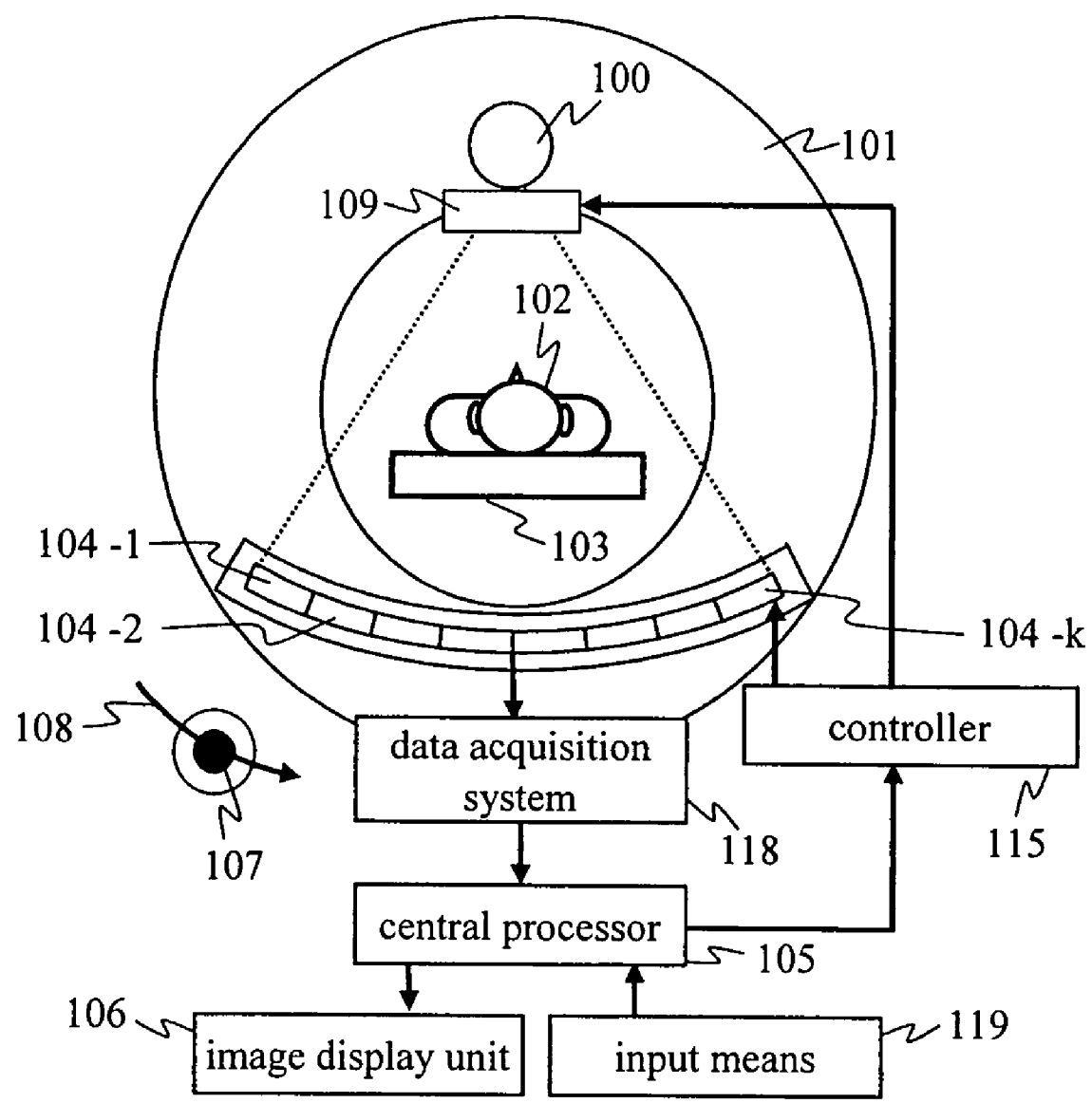
FIG. 1 schematically shows an example of an X-ray CT scanner according to the present invention.
Figure 2:
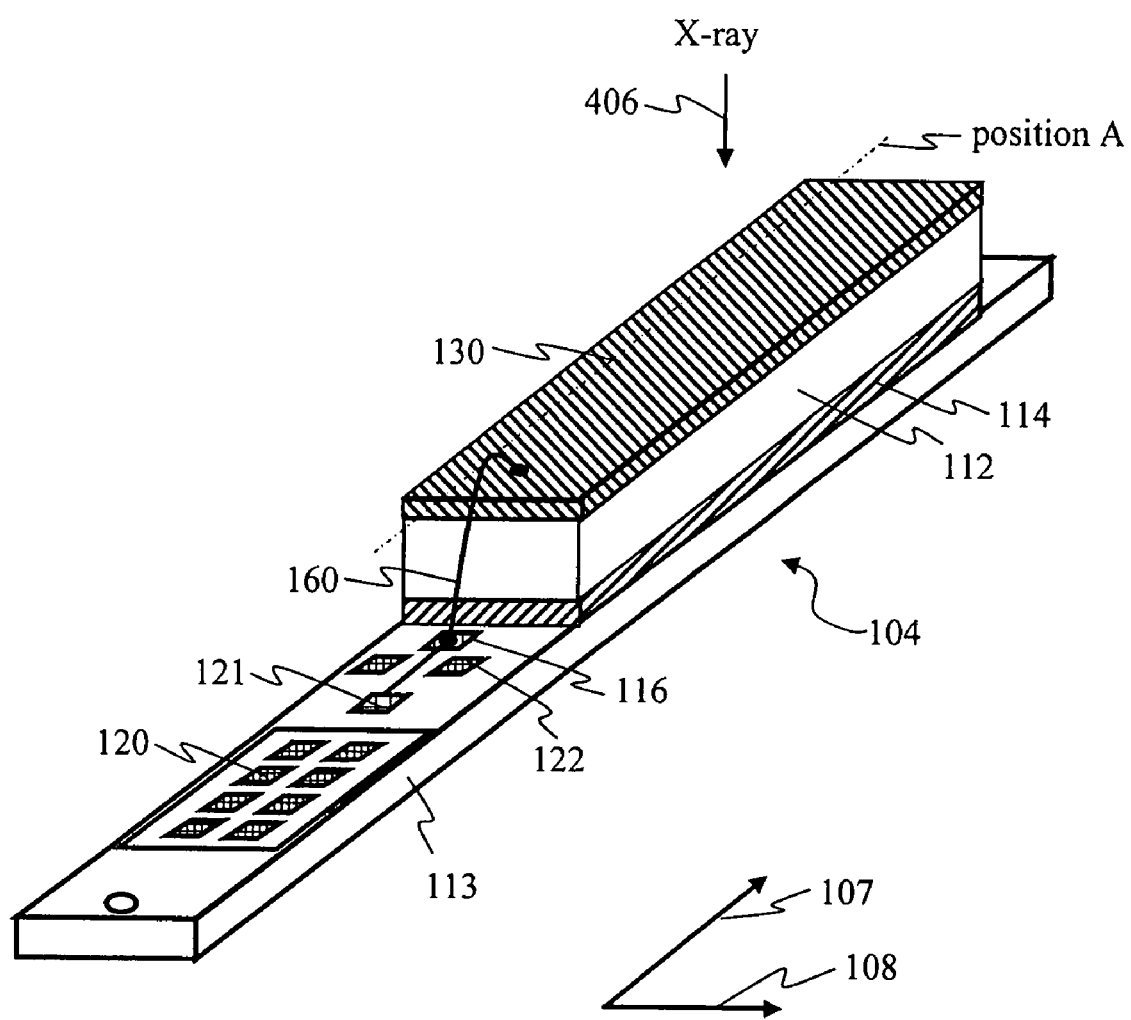
FIG. 2 shows an example of an X-ray detector according to the present invention.
Figure 3:
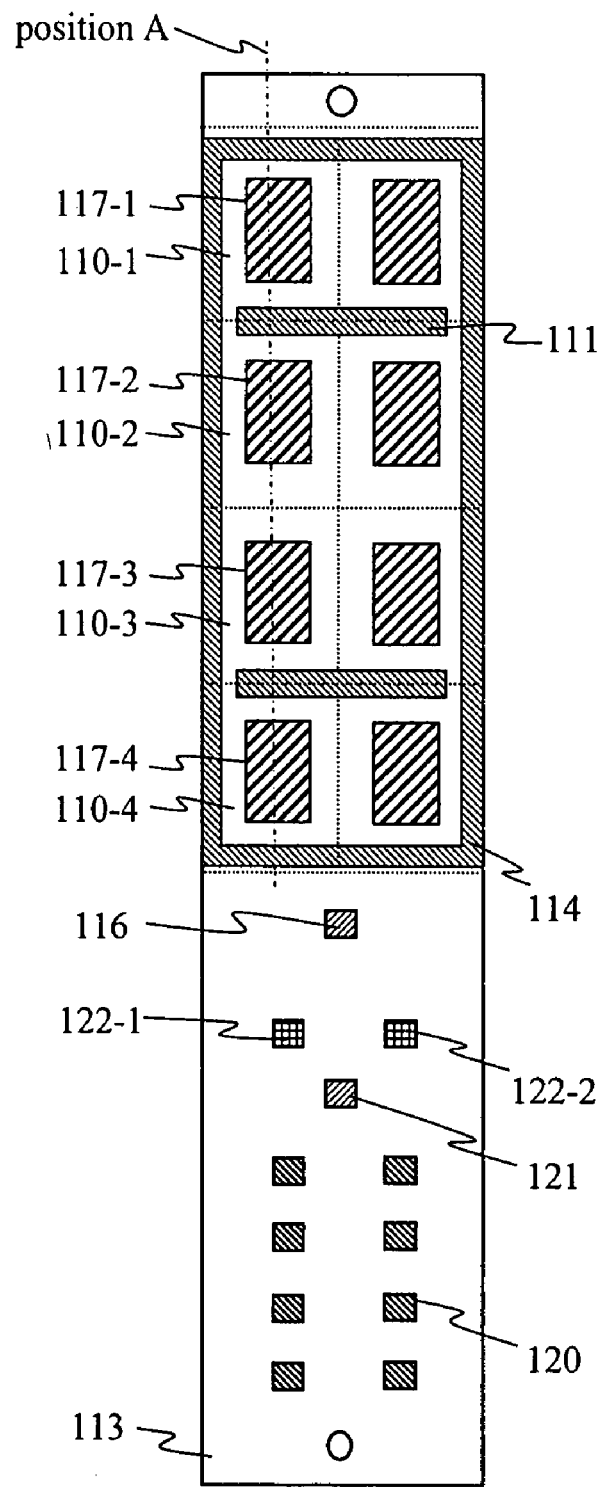
FIG. 3 shows the configuration of pixel electrodes and guard-ring electrodes formed on a distribution module.
Figure 4:
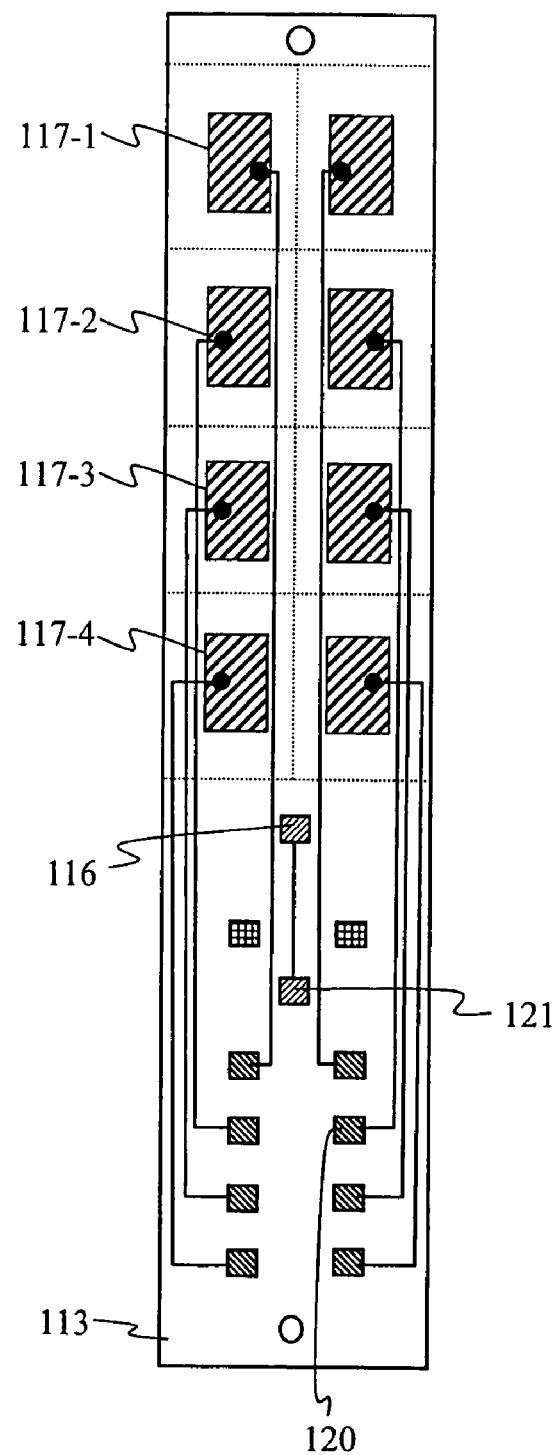
FIG. 4 shows an example of electric lines of the pixel electrodes and the guard-ring electrodes.
Figure 5:
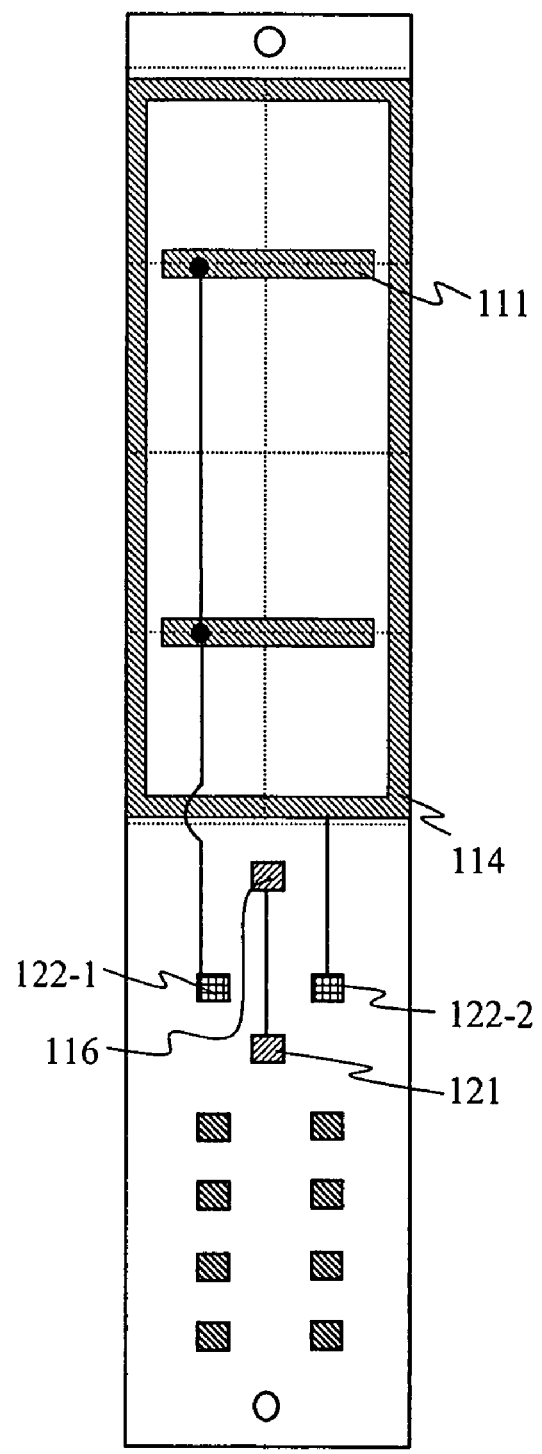
FIG. 5 shows an example of electric lines of the pixel electrodes and the guard-ring electrodes.
Figure 6:
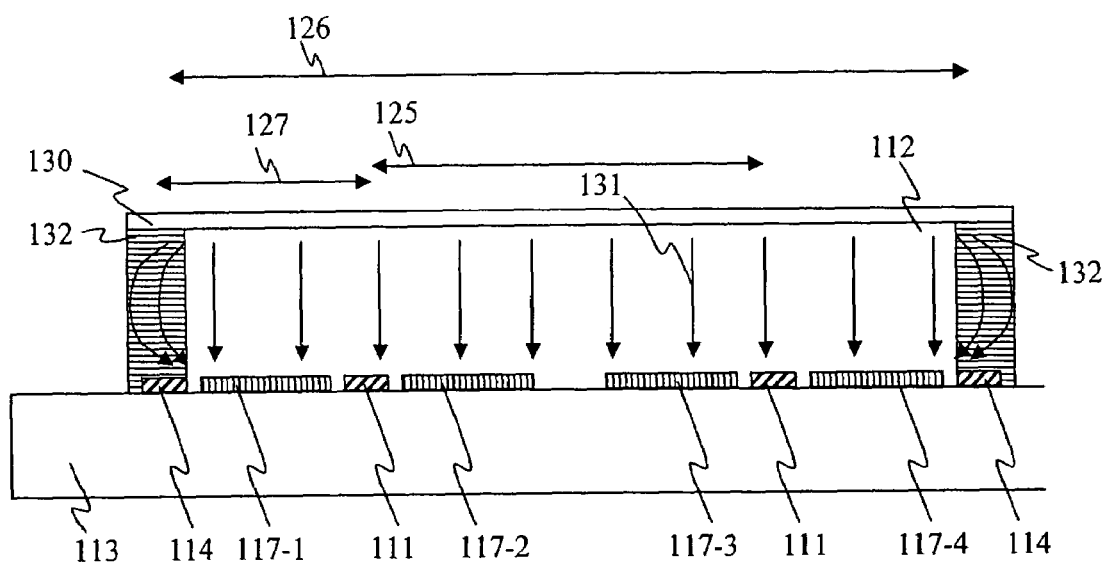
FIG. 6 shows a cross-sectional view taken along position A of FIG. 2 and FIG. 3.
Figure 7:
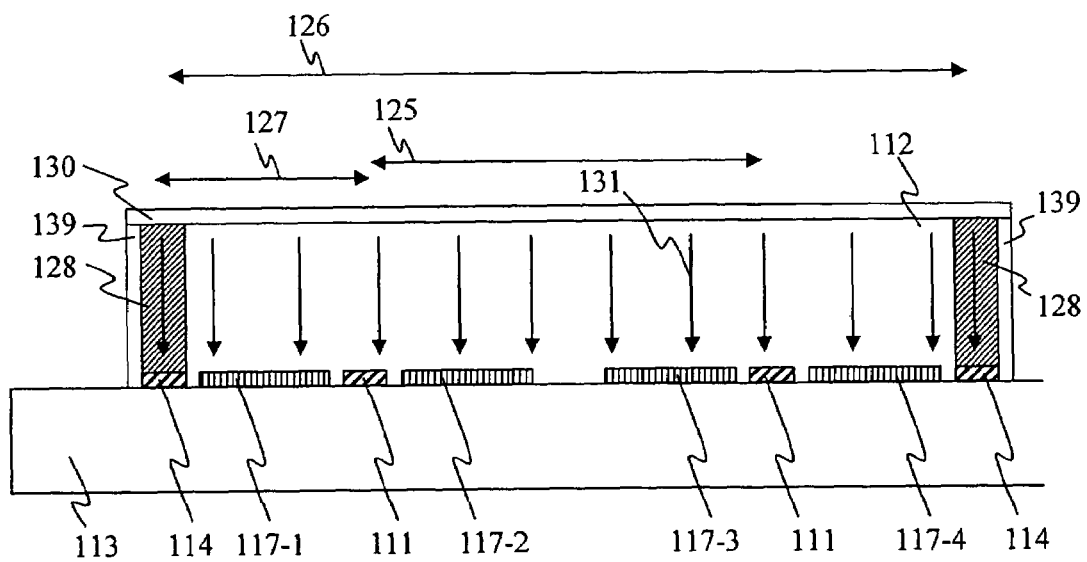
FIG. 7 shows a cross-sectional view taken along position A of FIG. 2 and FIG. 3.
Figure 8:
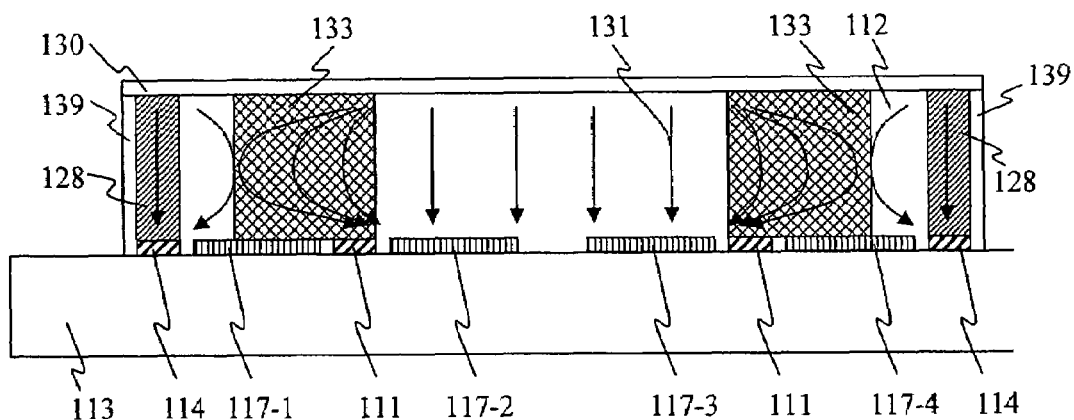
FIG. 8 shows the difference in electric field depending on the presence or absence of interelement guard-ring electrodes.
Figure 9:
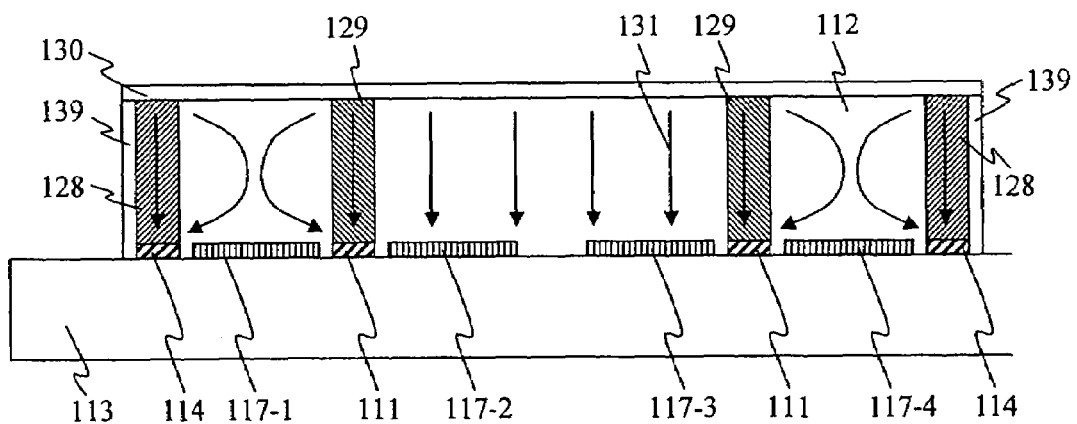
FIG. 9 shows the difference in electric field depending on the presence or absence of interelement guard-ring electrodes.
Figure 10:
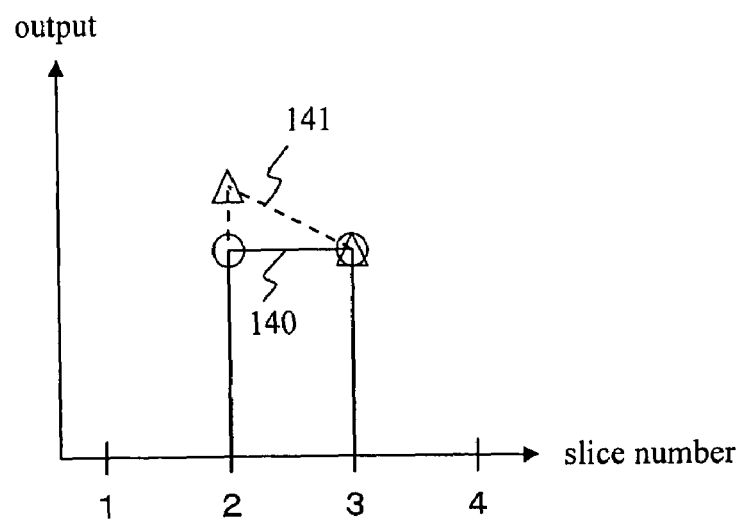
FIG. 10 shows the effect of the guard rings with respect to output images.
Figure 11:
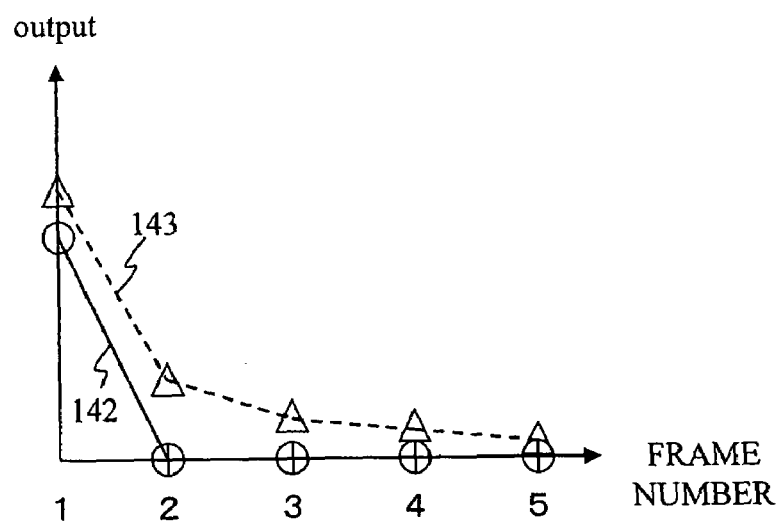
FIG. 11 shows the effect of the guard rings with respect to output images.

FIG. 1 schematically shows an X-ray CT scanner of the present embodiment. FIG. 2 is an example of an X-ray detector mounted on the X-ray CT scanner of FIG. 1. FIG. 3 shows the configuration of pixel electrodes and guard-ring electrodes formed on a distribution module 113. FIGS. 4 and 5 show an example of electric lines of the pixel electrodes and an example of electric lines of the guard-ring electrodes, respectively. FIGS. 6 and 7 show cross-sectional views taken along position A of FIGS. 2 and 3, and the figures show the difference in electric field, depending on the presence or absence of a peripheral guard-ring electrode 114. FIGS. 8 and 9 show the difference in electric field distribution, depending on the presence or absence of interelement guard-ring electrodes 111. FIGS. 10 and 11 show guard-ring effects with respect to output images.

As shown in FIG. 1, the X-ray CT scanner of the present embodiment comprises: an X-ray tube 100 for emitting X rays; a collimator 109 for limiting an X-ray irradiation field; an X-ray detector 104 for detecting X rays and converting the X-rays into electric signals; a data acquisition system 118 for acquiring signals from the X-ray detector 104; a central processor 105 for storing data from the data acquisition system 118 and conducting image processing; a image display unit 106 for displaying the results of the image processing; an input means 119 for conducting the setting for the start of imaging and the setting for the input of parameters; and a controller 115 for controlling the X-ray tube 100, the X-ray detector 104, the collimator 109, and a rotated gantry 101. A plurality of X-ray detectors 104 are disposed in an arc having the X-ray tube 100 approximately as its center (the number of the X-ray detectors 104 is k in the figure). Further, in the figure, while each of the X-ray detectors 104 has a structure such that X-ray detecting elements are disposed in the form of a matrix having four rows and two columns (four slices and two channels), the number of the X-ray detecting elements is used for ease of explanation; the present invention is not limited thereto.

The procedure of imaging will be described with reference to FIG. 1. First, the setting of imaging conditions is carried out with the input means 119. The X-ray CT scanner of the present embodiment has a function realizing a plurality of imaging FOV by changing the FOV size in the slice direction with which imaging is conducted, and the imaging FOV is selected in accordance with the setting. As one example of this selectable imaging FOV, the present embodiment includes imaging conditions; that is, the X-ray detector 104 has an FOV with a two-slice width and an FOV with a four-slice width. The X-ray detector of the present embodiment is a detector comprising four-slice X-ray detecting elements. Under the condition of the FOV with a four-slice width, signals are read from the X-ray detecting elements of all the slices, and in the case of the FOV with a two-slice width, signals are read from the X-ray detecting elements of the central two slices (the second slice and the third slice). In this case, the collimator 109 operates in accordance with the slice width of each FOV, so that the X-ray irradiation field is limited to the FOV with a corresponding slice width.

Next, when the start of imaging is inputted through the input means 119, the collimator 109 composed of a plurality of metal plates moves the metal plates, so as to limit the X-ray irradiation field depending on the imaging FOV conditions. These metal plates are made of lead, for example. After the irradiation field is determined, an object 102 on a bed 103 is irradiated with X rays from the X-ray tube 100. Part of the X rays penetrates the object 102, and it is then detected by the X-ray detecting elements of the X-ray detector 104. As a result, the X-ray detecting elements in accordance with the imaging FOV output an electric signal in accordance with the X-ray dose. This electric signal is subjected to an analog-to-digital conversion (A/D conversion) through the data acquisition system 118, and it is then converted into a digital signal.

In this imaging, a collection of digital signals obtained from the plurality of X-ray detecting elements that constitute the X-ray detector 104 forms one projection image. Further, an X-ray irradiation angle with respect to the object is changed by rotating the rotated gantry 101 equipped with the X-ray tube 100 and the X-ray detector 104 in a rotation direction 108, the projection image with a 360-degree field of view is obtained for each projection. This acquisition is conducted by every 0.4 degrees, for example. During the acquisition, the controller 115 controls the rotation of the rotated gantry 101 and the readout of the X-ray detector 104. The central processor 105 implements image processing or reconstruction with respect to the acquired projection images. The image processing is flat fielding correction processing or offset correction processing, for example. The results of the reconstruction are displayed on the image display unit 106.

One example of the X-ray detector 104 mounted on the X-ray CT scanner of the present invention will be described with reference to FIGS. 2 to 5. As shown in FIG. 1, a plurality of X-ray detectors 104 of FIG. 2 are aligned in the form of a circular arc and are disposed opposite to the X-ray tube 100, so that X rays become incident from a direction 406. Directions 107 and 108 shown in FIG. 2 are disposed so that they correspond to the direction of the axis of rotation 107 and the direction of rotation 108 shown in FIG. 1. As shown in FIG. 2, the X-ray detector 104 comprises a photoelectric conversion layer 112 for detecting X rays and generating electric signals and a distribution module 113 for reading the electric signals. This photoelectric conversion layer 112 is composed of a photoelectric conversion material such as amorphous selenium (a-Se), cadmium telluride (CdTe), cadmium zinc telluride (CdZnTe), or mercuric iodide ($HgI_2$), and it has a thickness of 100 to 1000 μm, for example. The photoelectric conversion layer 112 is structured so that it is sandwiched between a common electrode 130 formed thereon and a plurality of pixel electrodes (not shown in FIG. 2) formed on the distribution module 113.

As shown in FIG. 3, pixel electrodes 117 are separate electrodes, and one pixel electrode 117 and the common electrode 130 sandwich the photoelectric conversion layer 112, thereby forming one X-ray detecting element 110. The photoelectric conversion layer 112 in this region detects X rays and generates electrons and holes. In FIG. 3, the pixel electrode 117 in the j-th column (slice) is denoted by 117-j. Similarly, the corresponding X-ray detecting pixel element is denoted by 110-j. The electrons and holes generated in the photoelectric conversion layer 112 are individually moved to the electrodes by providing a potential difference between the pixel electrode 117 and the common electrode 130, and readout is then conducted. The potential difference varies depending on the material or application; for example, a film thickness of 1 μm corresponds to 1 mm to several hundred V. This is applied from electrode pads on the distribution module 113, and electric signals generated by the X rays are read. As one example of a structure to realize the above, based on the X-ray detector 104 of the present embodiment, as shown in FIG. 2, the common electrode 130 is electrically connected to an electrode pad 121 via a bonding wire 160 and an electrode pad 116, and electrode pads 120 are electrically connected to individual pixel electrodes 117 via electric lines, as shown in FIG. 4.

Further, as shown in FIG. 3, a peripheral guard-ring electrode 114 is provided along the periphery of the X-ray detector 104, and it is electrically connected to an electrode pad 122-2, as shown in FIG. 5. The peripheral guard-ring electrode is connected to ground potential, and thus a voltage is applied thereto. In this way, it is possible to improve electric-field uniformity and to prevent the inflow of electrical charges from the end portions of the photoelectric conversion layer 112. This will be described with reference to FIGS. 6 and 7.

FIG. 6 shows electric fields in cases in which the peripheral guard-ring electrode 114 is caused to be in a state of electrically open circuit (to be hereafter referred to as an "electrically open-circuit state"). This state includes cases in which the electric field generated between the peripheral guard-ring electrode 114 and the common electrode 130 is ignorable with respect to the electric field between the pixel electrodes 117 and the common electrode 130, such as cases in which the peripheral guard-ring electrode 114 is not connected to ground potential, cases in which the peripheral guard-ring electrode 114 is not provided, and cases in which the potential difference between the peripheral guard-ring electrode 114 and the common electrode 130 is ignorable, 10% or less, for example, with respect to a potential difference between the pixel electrodes 117 and the common electrode 130. In such cases, a current flowing between the peripheral guard-ring electrode 114 and the common electrode 130 is ignorable. In contrast, FIG. 7 shows electric fields in cases in which the peripheral guard-ring electrode 114 is connected to ground potential, and a voltage is applied thereto. In both figures, an arrow 131 represents an electric-field direction, and X rays become incident in the range indicated by an arrow 126 in the case of the FOV with a four-slice width and in the range indicated by an arrow 125 in the case of the FOV with a two-slice width. In FIG. 6, the electric fields 131 are distorted in the end regions 132; that is, non-uniformity is caused as compared with those in other portions. Consequently, the signals thus generated in the regions 132 flow into pixel electrodes 117-1 and 117-4. On the other hand, in FIG. 7, uniform electric fields 131 are generated between the electrodes in regions 128, and signals generated in the regions 128 and regions 139 (the regions 132 of FIG. 6) are read from the peripheral guard-ring electrode 114. Consequently, the inflow of signals into the pixel electrodes 117 is prevented. In the present embodiment, it is particularly desirable that the ground potential at which the peripheral guard-ring electrode 114 is connected be an electric potential equal to that of an adjacent pixel electrode or an electric potential having such level that the electric fields in the photoelectric conversion layer 112 are not significantly distorted.

Next, cases in which the imaging FOV is changed will be examined. While FIG. 7 shows the electric fields in the case of the FOV with a four-slice width, if this FOV is directly changed to the FOV with a two-slice width, since the pixel electrodes 117-1 and 117-4 that do not contribute readout are in the electrically open-circuit state, distorted electric fields are generated as shown in FIG. 8. In such case, electrical charges generated in regions 133 in particular are read by pixel electrodes 117-2 and 117-3. However, if the interelement guard-ring electrodes 111 are provided and connected to ground potential, the electric fields are changed as shown in FIG. 9. In this way, the distortion of the electric fields at the end portions of the pixel electrodes 117-2 and 117-3 is significantly reduced, uniformity is improved, and the signals generated in the X-ray detecting elements 110-1 and 110-4 are read by the interelement guard-ring electrodes 111. Thus, the inflow of signals into the X-ray detecting element 110-2 or 110-3 can be suppressed. Thus, by establishing the connection to ground potential prior to X-ray irradiation when the FOV with a two-slice width is selected, it becomes possible to remove/reduce the signals from the outside of the imaging FOV.

In the present embodiment, the pixel electrodes 117-1 to 117-4 are disposed at certain intervals in the slice direction 107. The width of each of the interelement guard-ring electrodes 111 disposed between adjacent pixel electrodes 117 in the slice direction is less than the width of each of the adjacent pixel electrodes 117 in the slice direction. Particularly, it is desirable that the width of each of the interelement guard-ring electrodes 111 in the slice direction be ignorable; that is, one tenth or less, for example, with respect to the width of each of the adjacent pixel electrodes 117 in the slice direction.

It is particularly desirable that a voltage at which the interelement guard-ring electrodes 111 are connected be an electrical potential equal to that of the adjacent pixel electrodes or an electrical potential that does not significantly distort the electrical fields in the photoelectric conversion layer 112. Further, even when the peripheral guard-ring electrode 114 and the interelement guard-ring electrodes 111 are connected to ground potential via a connection circuit, they are not connected to a readout circuit, and thus, the signals thereof are not read. Therefore, the signals read from the above electrodes are not used for creating reconstructed images.

Next, with reference to FIGS. 10 and FIG. 11, the influence of signals from the outside of the imaging FOV with respect to output images, and the effect of the interelement guard-ring electrodes 111 will be described. The case that will be examined hereafter is as follows: while X-ray irradiation was conducted so that X rays would be uniformly incident in the range indicated by the arrow 125 of FIG. 6 when imaging was conducted with the FOV having a two-slice width, but X rays resulted in being incident also in the range indicated by the arrow 127 due to X-ray scattering or the like from the object. The X-ray irradiation was conducted only in the first frame, and the subsequent frames were not irradiated with X rays. The vertical axis of each of the figures represents the output thus obtained. The horizontal axis of FIG. 10 represents slice numbers, and that of FIG. 11 represents continuously obtained frame numbers. White circles in the figures represent the output when the interelement guard-ring electrodes 111 are provided and connected to ground potential, and triangles in the figures represent the output when the interelement guard-ring electrodes 111 are caused to be in the electrically open-circuit state.

The output of the first frame will be examined. In cases in which no X rays are incident in the range 127, since X rays are considered to have uniformly become incident in the range 125, as shown in a profile 140 of FIG. 10, the output from the X-ray detecting element 110-2 and that from the X-ray detecting element 110-3 are equal. However, when the interelement guard-ring electrodes 111 are caused to be in the electrically open-circuit state, since a signal is also generated in the X-ray detecting element 110-1 due to X rays incident in the range 127, the signal from the X-ray detecting element 110-1 flows into the X-ray detecting element 110-2, and as a result, the signal from the X-ray detecting element 110-2 becomes greater than that from the X-ray detecting element 110-3, as indicated by a profile 141. Such phenomenon is referred to as a "cross-talk," which is a cause of the decrease in CT-value quantitative characteristics, the decrease in spatial resolution, or the occurrence of artifacts, in a reconstructed image. In contrast, when the interelement guard-ring electrodes 111 are provided and connected to ground potential, since the signals from the X-ray detecting element 110-1 are read by the interelement guard-ring electrodes 111, the cross-talk is reduced/removed, and as a result, an output approximately equal to a profile 140 can be obtained.

Next, the output from the second frame and the subsequent frames will be examined. When the interelement guard-ring electrodes 111 are provided and connected to ground potential, since there are no incident X rays, the output is zero as indicated by a profile 142 of FIG. 11. However, when the interelement guard-ring electrodes 111 are caused to be in the electrically open-circuit state, the output is not zero, as indicated by a profile 143. This is because that electrical charge signals generated in a weak electric field region in the X-ray detecting element 110-1 or the like are gradually read. Namely, the cross-talk remains in the subsequent frames. Due to such phenomenon, the decrease in CT-value quantitative characteristics, the decrease in time resolution, or the occurrence of artifacts is caused. In contrast, by providing the interelement guard-ring electrodes 111 and connecting them to ground potential, such signals can be reduced or removed, and as a result, an output approximately equal to the profile 142 can be obtained.

In contrast, in the case of the FOV with a four-slice width, when the influence of the cross-talk between the X-ray detecting elements 110 is small with respect to reconstructed images or when it is possible to reduce the influence through correction processing, reconstruction, or the like, it is desirable that the interelement guard-ring electrodes 111 be caused in the electrically open-circuit state and obtain signals in the regions 129. In this way, it becomes possible to reduce unnecessary radiation exposure and increase the amount of signal. Namely, since the SNR is improved, noise of the reconstructed image is reduced, and image quality can be improved.

Thus, the function of changing the location or the presence/absence of the guard rings by changing the connection of the interelement guard-ring electrodes 111 to ground potential depending on imaging conditions is effective in reducing unnecessary radiation exposure or improving image quality. Thus, based on the X-ray detector 104 of the present embodiment, by changing the connection of the interelement guard-ring electrodes 111 to ground potential depending on the imaging FOV, it is possible to realize the effects of improving CT-value quantitative characteristics, improving time resolution/spatial resolution, reducing/removing artifacts, reducing unnecessary radiation exposure, and improving image quality due to reduction in reconstructed image noise.

While the guard-ring electrodes are provided only in the slice direction in the present embodiment, the present invention is not limited thereto. The present invention can also be applied to cases in which the X-ray irradiation field varies in the channel direction. In such case, the guard-ring electrodes may be provided between X-ray detecting elements adjacent in the channel direction, so as to change the earthing of the applied voltage. Further, the present invention may be applied to cases in which the switching of earthing is conducted in both directions.

While the guard-ring electrodes 111 and 114, and the pixel electrodes 117 are provided in a location sandwiched between the photoelectric conversion layer 112 and the distribution module 113 in the present embodiment, the present invention is not limited thereto. The guard-ring electrodes 111 and 114 and the pixel electrodes 117 may be provided on the upper surface of the photoelectric conversion layer 112. In such case, the common electrode 130 is provided in a location sandwiched between the photoelectric conversion layer 112 and the distribution module 113.

While the pixel electrodes 117 are disposed at certain intervals in the slice direction 107 and the width thereof is also constant in the present embodiment, the present invention is not limited thereto. The pixel electrodes 117 may be structured so that the pixel electrodes corresponding to the center of the detector are smaller than those corresponding to the end portions of the detector; the second and the third slice have a pitch of 1 mm and the first and the fourth slice have a pitch of 2 mm, for example. Also, the width of the pixel electrodes 117 at the center of the detector in the slice direction may be thinner but thicker at the end portions of the detector. In such case, while the guard-ring electrodes 111 are adjacent to the pixel electrodes 117 each having a different width, it is desirable that the width of the guard-ring electrodes 111 be less, sufficiently smaller in particular, than the pixel electrode 117 having the smaller width. Furthermore, the present invention may include cases in which the pixel electrodes 117 are disposed at irregular intervals in various locations and cases in which the width of each of the pixel electrodes 117 is different from each other.

While the X-ray detector is a direct-detection-type detector in the present embodiment, an indirect-type detector may be used. In such case, an indirect-type detector has a structure such that it has a scintillator, such as cesium iodide or GOS ($Gd_2O_2S$: Tb), on the upper surface of the photoelectric conversion layer 112 composed of material such as crystal/poly/amorphous silicon. In the detection, the photoelectric conversion layer 112 detects light generated by the scintillator and converts the light into an electric signal. Thus, the thickness of the photoelectric conversion layer 112 is less than that of the direct-type detector; it is 50 nm to several μm, for example. Further, the common electrode 130 is composed of a transparent conductor, such as an ITO film (indium-tin oxide film) or a tin oxide ($SnO_2$) film, for the transmission of the light generated by the scintillator.

Embodiment 2

Figure 12:
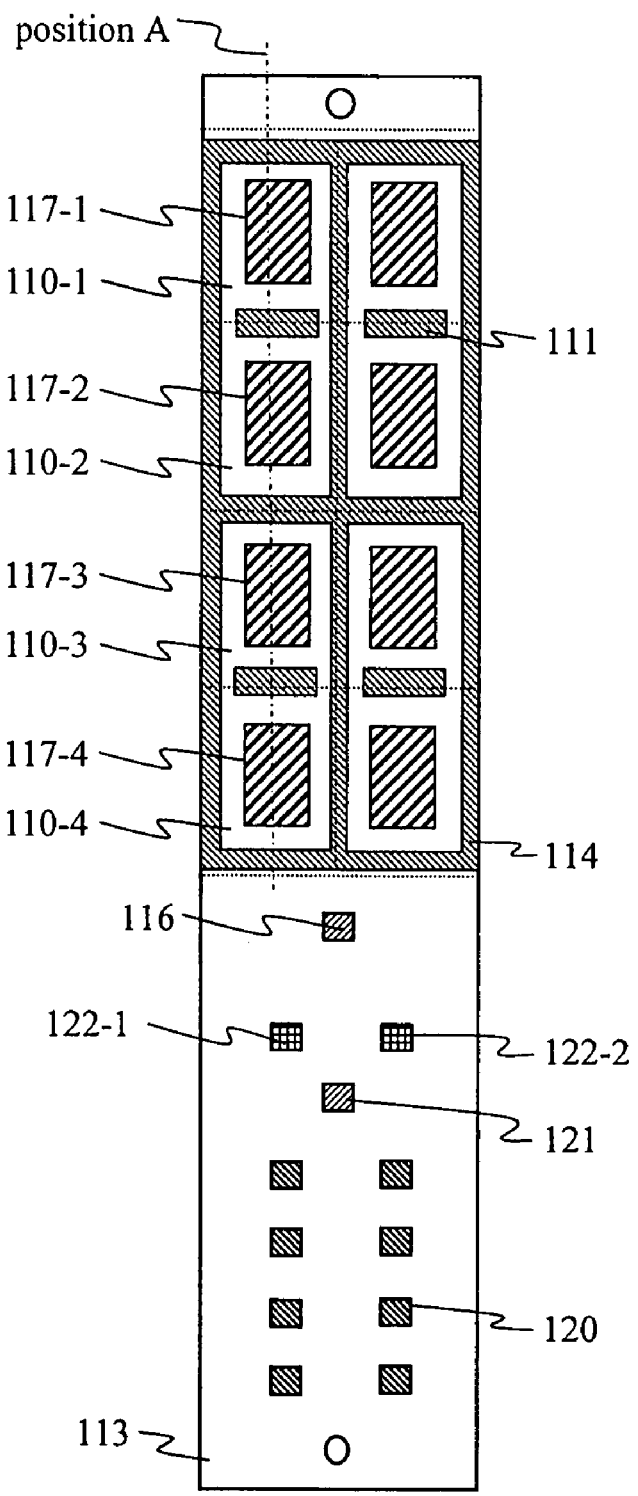
FIG. 12 shows an example of the configuration of guard-ring electrodes of the X-ray detector.
Figure 13:
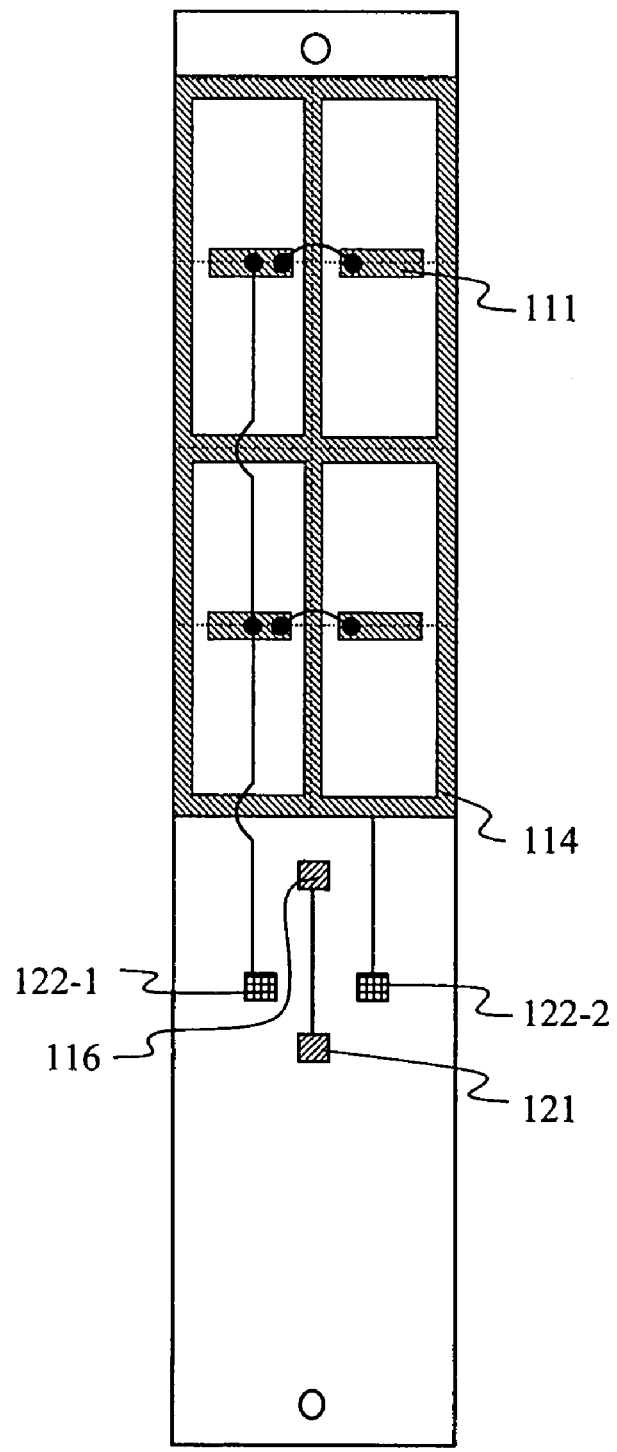
FIG. 13 shows an example of electric lines of the guard-ring electrodes.
Figure 14:
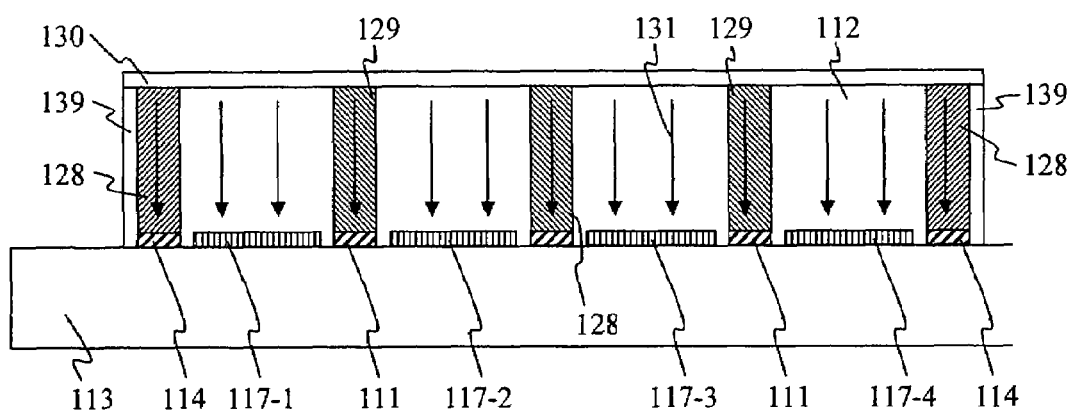
FIG. 14 shows a cross-sectional view explaining the appearance of electric fields when binning is present and absent.
Figure 15:
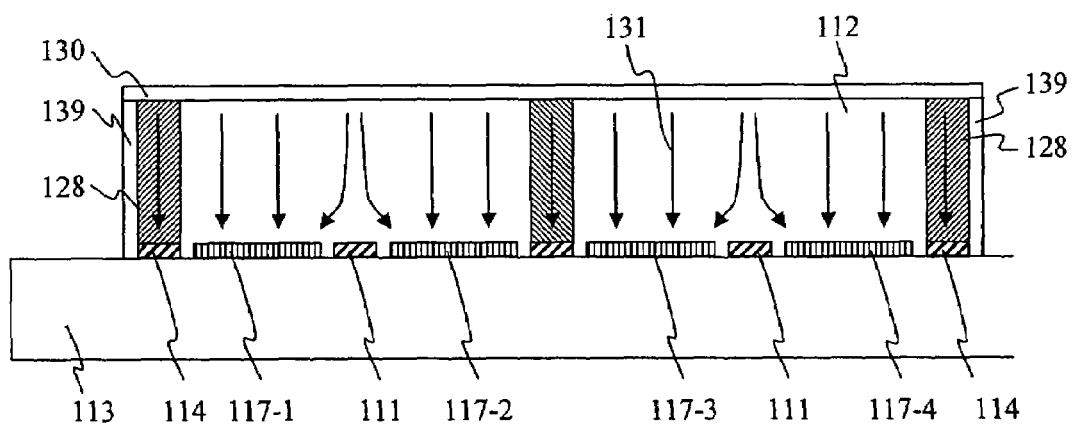
FIG. 15 shows a cross-sectional view explaining the appearance of electric fields when binning is present and absent.

An X-ray CT scanner of the present embodiment is the same as that described with FIG. 1 in Embodiment 1, and the structure of the X-ray detector 104 is also the same as that described with FIG. 2 in Embodiment 1. FIG. 12 shows an example of the configuration of the guard-ring electrodes of the X-ray detector 104 according to the present embodiment. FIG. 13 shows an example of electric lines of the guard-ring electrodes of FIG. 12. The X-ray CT scanner of the present embodiment comprises a function (binning) of adding signals from adjacent X-ray detecting elements and is capable of changing the position or the presence/absence of the guard rings, depending on binning conditions. FIG. 14 and FIG. 15 show cross-sectional views explaining the appearance of electric fields when the binning is present and absent.

Hereafter, as one example of imaging conditions involving different kinds of binning, no-binning imaging in which binning is not conducted, and two-pixel binning imaging in which binning is conducted on the signals from the first slice and the second slice and on the signals from the third slice and the fourth slice will be described. The binning is conducted by an analog signal adding circuit in the data acquisition system 118 shown in FIG. 1.

As shown in FIG. 12, the peripheral guard-ring electrode 114 is provided so that it surrounds the pixel electrodes 117 on which binning is conducted, and the interelement guard-ring electrodes 111 are provided between the pixel electrodes 117. As shown in FIG. 4 in Embodiment 1, the pixel electrodes 117 are electrically connected to the electrode pads 120, and the guard-ring electrodes are electrically connected to the electrode pads 122-1 and 122-2, as shown in FIG. 13. Ground potential is applied to the peripheral guard-ring electrode 114, without being changed depending on binning conditions. It is desirable that the ground potential be equal to a voltage applied to the pixel electrodes.

FIG. 14 and FIG. 15 show cross-sectional views taken along position A of FIG. 12. FIG. 14 shows cases in which the no-binning imaging is conducted, and FIG. 15 shows cases in which the two-pixel binning imaging is conducted. In the case of the no-binning imaging, the interelement guard-ring electrodes 111 are connected to ground potential and a voltage is applied thereto, so as to use them as guard rings. In this way, signals in the regions 129 of FIG. 14 are read from the interelement guard-ring electrodes 111. Further, the peripheral guard-ring electrode 114 reads signals in the regions 128 and 139. Based on these guard-ring electrodes, the cross-talk between the individual X-ray detecting elements 110 can be reduced. Herein, while the peripheral guard-ring electrode 114 and the interelement guard-ring electrodes 111 are connected to a voltage applying circuit, they are not connected to the readout circuit. Thus, the signals read from these electrodes are not used for creating reconstructed images.

In contrast, in the case of the two-pixel binning imaging, the electrically open-circuit state is required by using a method in which the interelement guard-ring electrodes 111 are not connected to ground potential, for example. In such case, the electric field in the region between the X-ray detecting elements 110-1 and 110-2 and the electric field in the region between the X-ray detecting elements 110-3 and 110-4 are somewhat distorted, as shown in FIG. 15. Accordingly, the signals generated by X rays incident in the regions corresponding to the regions 129 shown in FIG. 14 are drawn to adjacent pixel electrodes 117 and then read. As a result, signals including the signals in the regions can be obtained from the pixel electrodes 117. In this two-pixel binning imaging, since two X-ray detecting elements are considered to be one X-ray detecting element, no guard rings are necessary between the two X-ray detecting elements. Thus, it is desirable that the signals between these X-ray detecting elements 110 be detected and used.

The amount of increase in signal in cases in which the signals between the X-ray detecting elements 110 are also detected and used will be roughly estimated. For example, on the condition that the distance between centers of one X-ray detecting element 110 and its adjacent X-ray detecting element 110 in the slice direction is 1 mm; the slice width of each of their pixel electrodes 117 is 0.8 mm; the interelement guard-ring electrodes 111 each have a width of approximately 0.2 mm are provided in the space of 0.2 mm between the pixel electrodes 117; while the effective slice width is 1.6 mm after binning if the guard ring is conducted, if the guard ring is not conducted, a slice width of 1.8 mm can be realized, and thus, it becomes possible to realize an increase in the amount of signal by about 12.5%. Thus, in the case of binning, by not connecting the interelement guard-ring electrodes 111 to ground potential, it is possible to obtain more signals than in cases in which binning is simply conducted. Consequently, it is possible to improve the SNR and reduce unnecessary radiation exposure.

While the addition of the detector signals is conducted through analog signal addition by the data acquisition system 118 in the present embodiment, the present invention is not limited thereto. The present invention includes cases in which averaging processing or weighted summation is conducted in the data acquisition system 118 and cases in which these processings are conducted in the X-ray detector 104. Further, digital signal addition, averaging processing, weighted summation, or the like may be conducted with respect to AD-converted signals.

While the binning is conducted only in the slice direction in the present embodiment, the present invention is not limited thereto. The binning may be conducted in the channel direction. In such case, the interelement guard-ring electrodes 111 are provided between the pixel electrodes 117 adjacent to each other in the channel direction.

Figure 16:
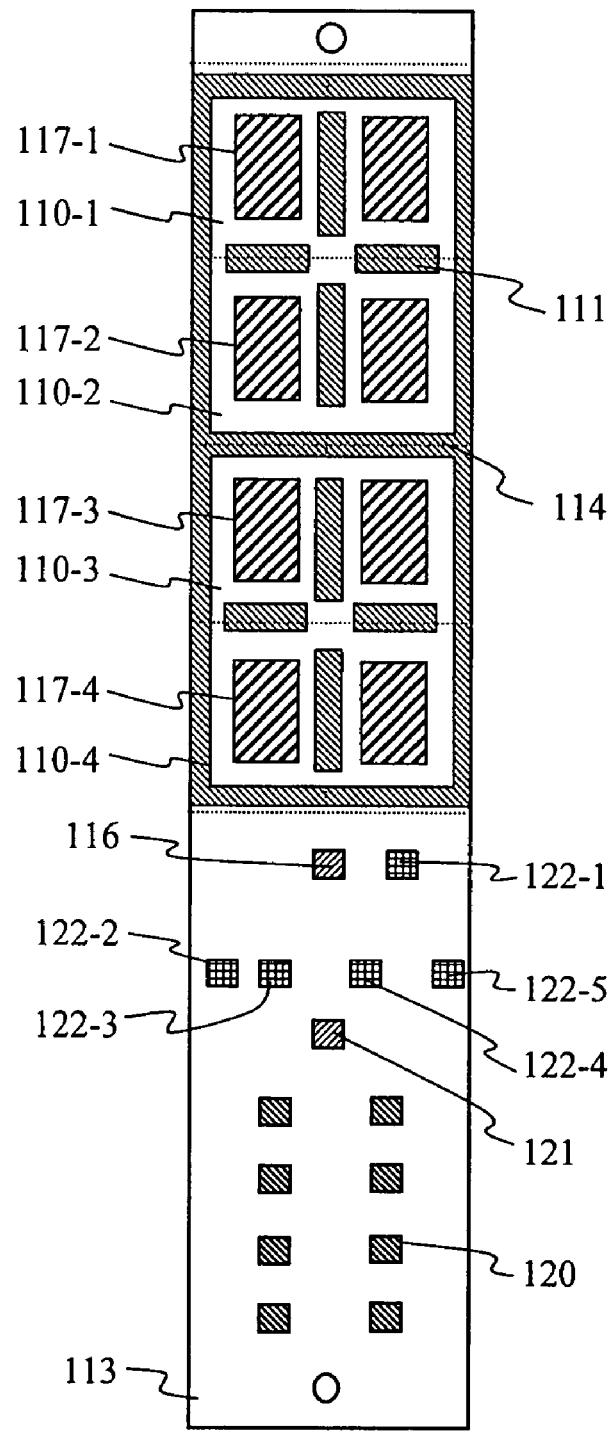
FIG. 16 shows an example of a distribution module.
Figure 17:
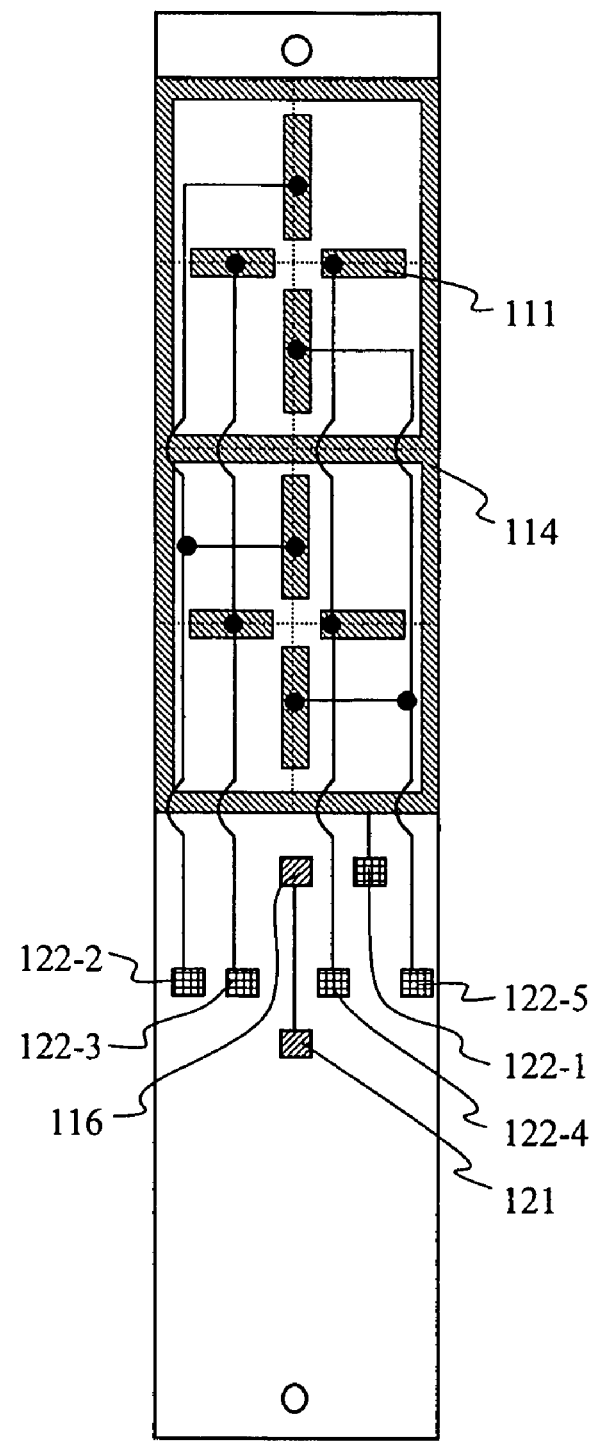
FIG. 17 shows an example of electric lines of guard-ring electrodes.

Further, the present invention includes cases in which the binning is conducted in both channel and slice directions. FIG. 16 shows one example of the distribution module 113 with which such binning is realized. In the example shown in FIG. 16, four of the pixel electrodes 117 are provided with one peripheral guard-ring electrode 114, and the interelement guard-ring electrodes 111 are provided among these four pixel electrodes 117. As shown in FIG. 17, these guard-ring electrodes are individually and electrically connected to the electrode pads 122, and an electrode pad 122-1 is always connected to ground potential. In cases in which imaging is conducted with such structure and binning is not conducted, all the electrode pads 122-2 to 122-5 are connected to ground potential. In the case of the binning in the slice direction, while the signal addition of slice 1 and slice 2 and the signal addition of slice 3 and slice 4 are conducted, control is exerted so that the electrode pads 122-2 and 122-5 are connected to ground potential but the electrode pads 122-3 and 122-4 are not connected to ground potential. In the case of the binning in the channel direction, while the signal addition of the adjacent channels is conducted, control is exerted so that the electrode pads 122-3 and 122-4 are connected to ground potential but the electrode pads 122-2 and 122-5 are not connected to ground potential. In the case of the four-pixel binning, control is exerted so that all the electrode pads 122-2 to 122-5 are not connected to ground potential.

With such ground potential switching control, when the binning is not conducted, the cross-talk between the individual pixel elements can be suppressed, and when the binning is conducted in the slice direction, it is possible to suppress the cross-talk between the pixel elements in the channel direction and to read X-ray signals incident between the pixel elements on which the binning is conducted. When the binning is conducted in the channel direction, it is possible to suppress the cross-talk between the pixel elements in the slice direction and to read X-ray signals incident between the pixel elements on which the binning is conducted. In the case of the four-pixel binning, it is possible to read X-ray signals incident between the individual pixel elements on which the binning is conducted. Based on such control, it is possible to obtain signals between pixel elements that correspond to the binning position.

While the position or the presence/absence of the guard rings is changed depending on binning conditions in the present embodiment, the present invention includes cases in which the position or the presence/absence of the guard rings is changed depending on the imaging FOV, as in Embodiment 1.

Embodiment 3

An X-ray CT scanner of the present embodiment is the same as that shown in FIG. 1 described in Embodiment 1. Based on the X-ray CT scanner in Embodiment 2, while the interelement guard-ring electrodes 111 are not connected to the readout circuit, in the present embodiment, the interelement guard-ring electrodes 111 can be connected to the readout circuit, and switching between the connection to ground potential and the connection to the readout circuit is made possible, depending on binning conditions.

Figure 18:
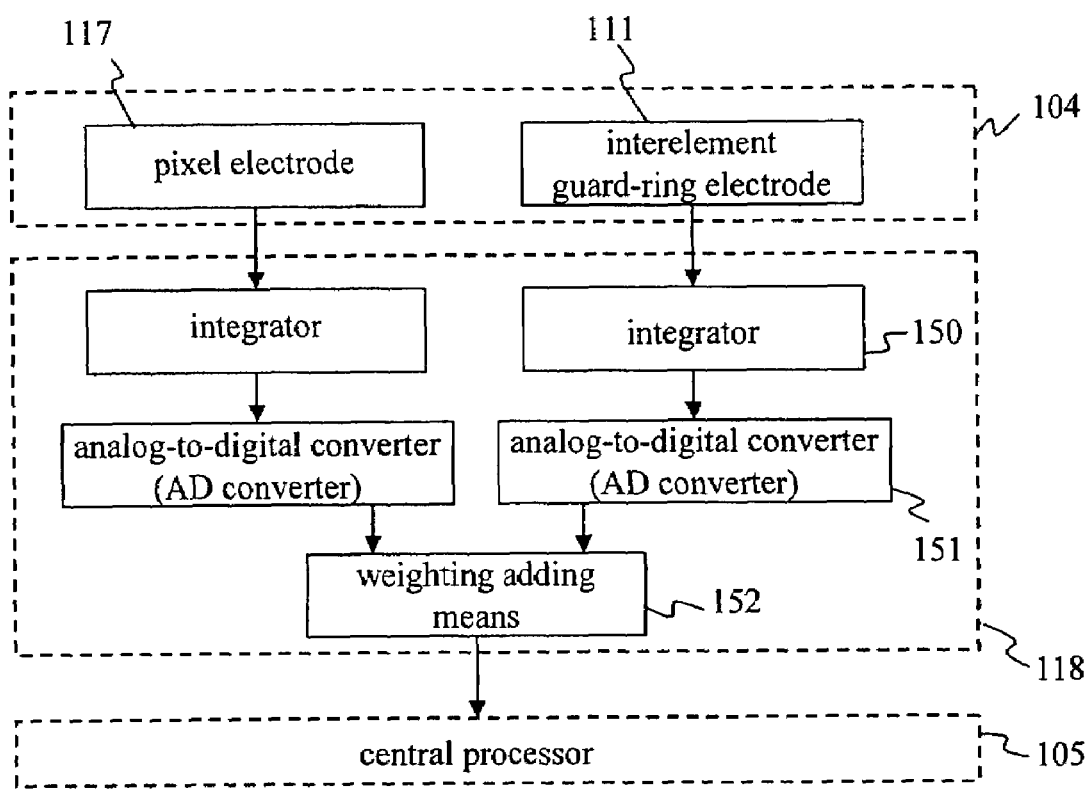
FIG. 18 shows an example of processing by a data acquisition system.

Based on the X-ray CT scanner of the present embodiment, when the binning is not conducted, the interelement guard-ring electrodes 111 are connected to ground potential. In contrast, when the binning is conducted, the interelement guard-ring electrodes 111 are connected to the readout circuit in the data acquisition system 118. FIG. 18 shows an example of the processing of the data acquisition system 118 in such case. As shown in FIG. 18, the output signals from the pixel electrodes 117 and the interelement guard-ring electrodes 111 are each subjected to a predetermined time integration by an integrator 150 and are then converted into voltage signals. The voltage signals are converted into digital signals by an analog-to-digital converter (AD converter) 151. Using the digital signals, weighted summation is conducted with respect to the signals from the pixel electrodes 117 on which the binning is conducted and the interelement guard-ring electrodes 111 between the pixel electrodes 117 by a weighting adding means 152. The weighting coefficient is uniformly 1 to each signal, for example. The signals on which the weighted summation has thus been conducted are outputted to the central processor 105.

Based on such operation, when the binning is not conducted, the interelement guard-ring electrodes 111 can suppress the cross-talk between the X-ray detecting elements 110. When the binning is conducted, it is possible to obtain signals including detected X-ray signals that are incident on the interelement guard-ring electrodes 111.

While the weighted summation of the digital signals is conducted in the data acquisition system 118 in the present embodiment, the present invention is not limited thereto. A weighting adder may be provided after the integrator 150 so as to conduct the weighted summation in an analog manner and then conduct AD conversion by the AD converter 151. Further, the present invention may include cases in which the data acquisition system 118 does not conduct the processing of the weighting adding means, digital signals are outputted to the central processor 105, the central processor 105 conducts correction processing, and the weighting adding means is carried out with respect to the digital signals.

While a uniform weighted summation is conducted in the present embodiment, the present invention is not limited thereto. For example, various types of weighted summation may be possible, including such addition that the SNR of the pixel electrodes 117 on which the binning is conducted and that of the interelement guard-ring electrodes 111 are the same ratio. Furthermore, a processing in which a value after the weighted summation is compressed is also included.

While the same integrator 150 and AD converter 151 are used for the pixel electrodes 117 and the interelement guard-ring electrodes 111 in the present embodiment, the present invention is not limited thereto. Various cases are possible, including cases in which the integral capacitance of the integrator 150 is different depending on the ratio of the area of the pixel electrodes 117 to that of the interelement guard-ring electrodes 111, cases in which an integrator having circuit noise smaller than that of the pixel electrodes 117 is used for the interelement guard-ring electrodes 111 that are presumed to have a small output based on the area ratio, cases in which the bit count of the AD converter is different, and cases in which the AD conversion ratio of the AD converter (the ratio of output to input voltage) is different.

Embodiment 4

Figure 19:
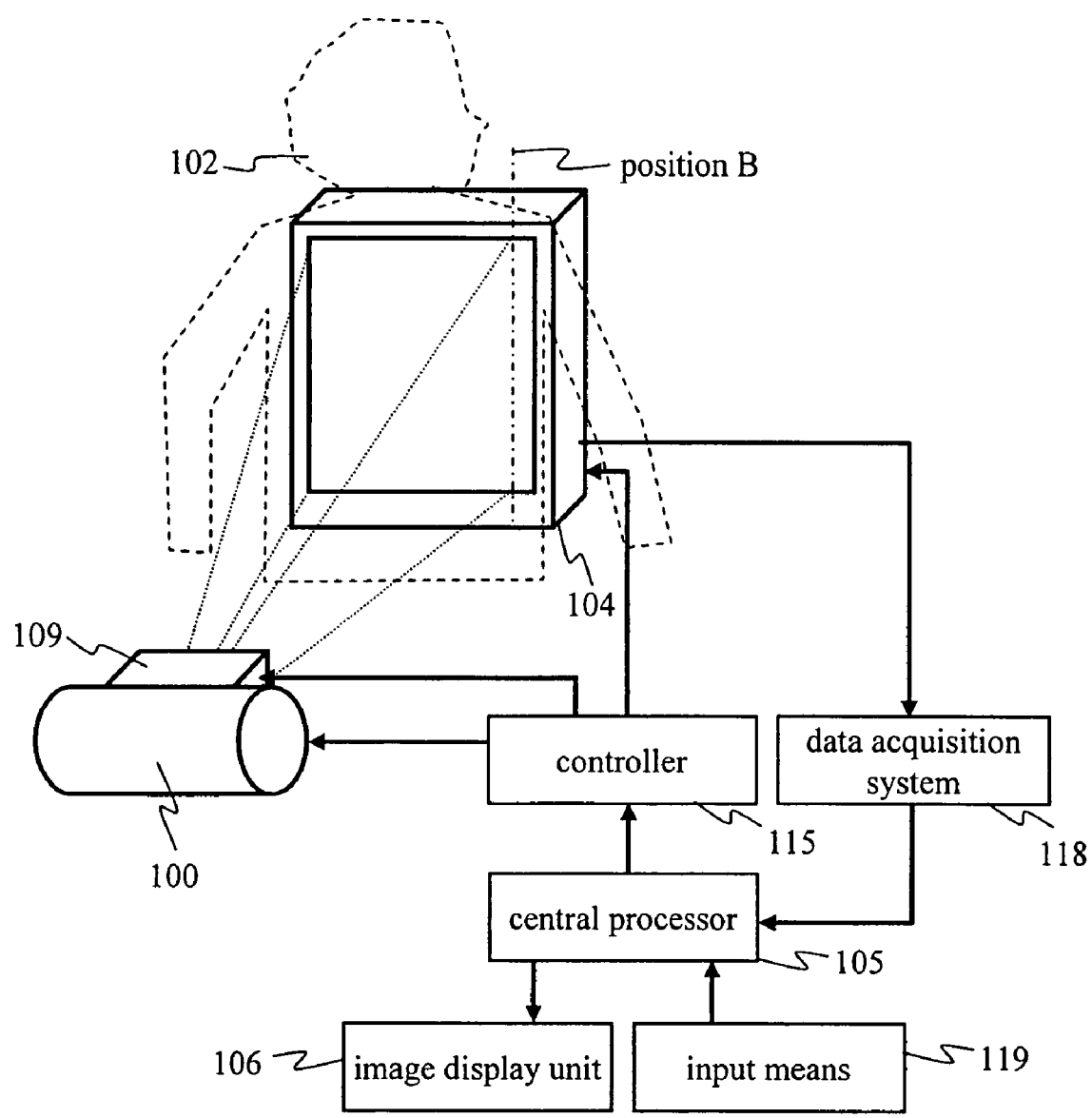
FIG. 19 shows an example of an X-ray digital radiography system.
Figure 20:
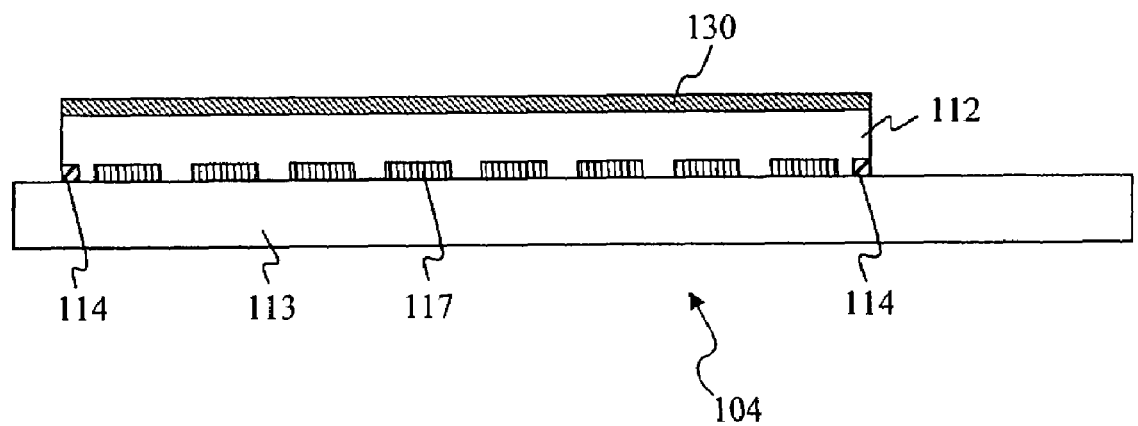
FIG. 20 shows a cross-sectional view of the structure of an X-ray detector.
Figure 21:
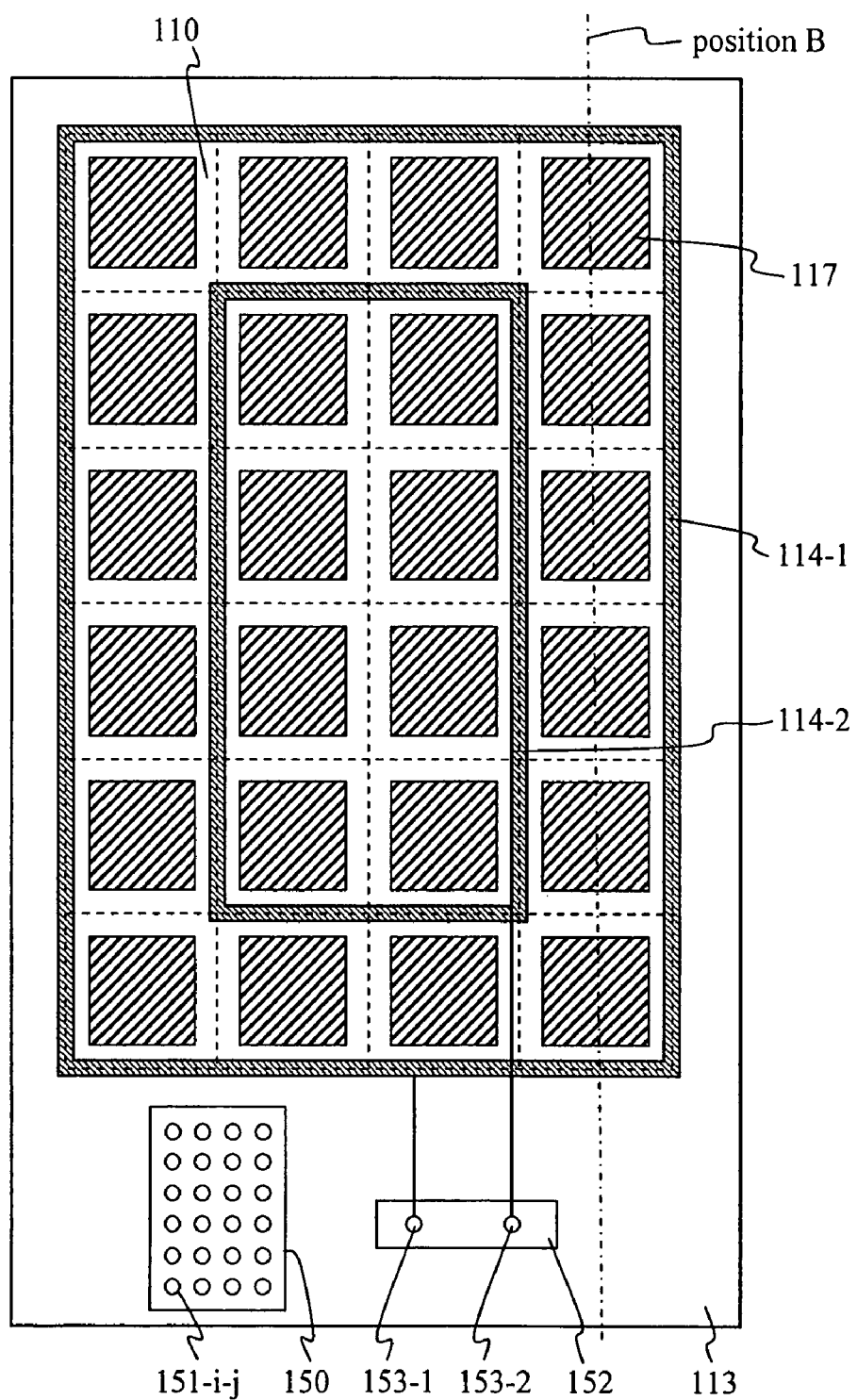
FIG. 21 shows the configuration of pixel electrodes and peripheral guard-ring electrodes.

The present embodiment relates to an X-ray digital radiography system equipped with a flat panel detector. FIG. 19 shows an example of the X-ray digital radiography system of the present embodiment. FIG. 20 shows a cross-sectional view with which the structure of the X-ray detector 104 of FIG. 19 is explained. FIG. 21 shows an explanatory diagram of the configuration of the pixel electrodes 117 and the peripheral guard-ring electrodes 114 formed on the distribution module 113 of the X-ray detector 104 of FIG. 20. While the flat panel detector 104 shown in the figure is provided with X-ray detecting elements 110 in a matrix form having six rows and four columns, the number of the X-ray detecting elements 110 is merely an example; the present invention is not limited thereto.

As shown in FIG. 19, the X-ray digital radiography system of the present embodiment comprises: an X-ray tube 100 for emitting X rays; a collimator 109; an X-ray detector (flat panel detector) 104 for detecting X rays and converting the X rays into electric signals; a data acquisition system 118 for acquiring signals from the flat panel detector 104; a central processor 105 for storing data from the date acquisition system 118 and performing image processing; an image display unit 106 for displaying the results of the image processing; an input means 119 for allowing the entry for the start of imaging or the setting of parameters; and a controller 115 for controlling the X-ray tube 100, the collimator 109, and the flat panel detector 104, as a basic configuration.

When conducting imaging, first, the start of imaging is inputted with the input means 119, and an object 102 is irradiated with X rays from the X-ray tube 100. Part of the X rays penetrates the object 102 and is then detected by the X-ray detector 104, which generates an electric signal depending on the X-ray amount. This electric signal is AD-converted by the data acquisition system 118, and a digital signal is thus obtained. In this imaging, a collection of digital signals obtained from many X-ray detecting elements of the X-ray detector 104 forms one projection image. Next, with respect to the digital signals of the X-ray detection signals, image processing is implemented by the central processor 105. The processing is a flat fielding correction processing or an offset correction processing, for example. An image thus obtained is displayed on the image display unit 106. The X-ray digital radiography system changeably enables either radiography by which one projection image is taken or fluoroscopy by which projection images are continuously taken.

Based on the X-ray detector 104 of the present embodiment, as shown in FIG. 20, a photoelectric conversion layer 112 is formed on the distribution module 113 on which the pixel electrodes 117 and the peripheral guard-ring electrodes 114 are formed, the common electrode 130 is formed on the upper surface of the photoelectric conversion layer 112, and the X-ray detecting elements 110 are formed with respect to the individual pixel electrodes 117. The pixel electrodes 117 and the peripheral guard-ring electrodes 114 are disposed as shown in FIG. 21. Namely, the pixel electrodes 117 are disposed in a matrix form having six rows and four columns. A peripheral guard-ring electrode 114-1 is formed so that all the X-ray detecting elements 110 are surrounded thereby, and an peripheral guard-ring electrode 114-2 is formed so that the central X-ray detecting elements 110 in a matrix form having four rows and two columns are surrounded thereby. The number of rows and columns of the X-ray detecting elements 110 is merely an example, and thus, the present invention is not limited thereto. Further, the output from the pixel electrode 117 in the j-th row and i-th column is electrically connected to a terminal 151-$i$-$j$ of a connector 150, and the peripheral guard-ring electrodes 114-1 and 114-2 are connected to terminals 153-1 and 153-2 of a connector 152, respectively.

The X-ray imaging system has an imaging function of switching two imaging FOV; that is, between a region A surrounded by the peripheral guard-ring electrode 114-1 and a region B surrounded by the peripheral guard-ring electrode 114-2. For example, when conducting imaging, the region A is used in the case of the radiography and the region B is used in the case of the fluoroscopy. This switching of the imaging FOV is conducted with the input means 119. When the region A is selected, based on the controller 115, the collimator 109 operates so that the X-ray irradiation field is limited in the range of the region A. Further, the controller 115 connects the terminal 153-1 of the connector 152 to ground potential, and the peripheral guard-ring electrode 114-1 guard-rings the inflow of signals into the X-ray detecting elements 110 in the region A from the outside thereof. The output of these X-ray detecting elements 110 is outputted to the data acquisition system 118 from the terminal 151-$i$-$j$ of the connector 150. On the other hand, when the region B is selected, based on the controller 115, the collimator 109 operates so that the X-ray irradiation field is limited in the range of the region B. Further, the controller 115 connects the terminal 153-2 of the connector 152 to ground terminal, and the peripheral guard-ring electrode 114-2 guard-rings the inflow of signals into the X-ray detecting elements 110 in the region B from the outside thereof. The output from the X-ray detecting elements 110 in the region B is outputted to the data acquisition system 118 from the terminal 151-$i$-$j$ of the connector 150. In such case, the pixel electrodes 117 of the X-ray detecting elements 110 outside the region B are not electrically connected to the readout circuit; that is, they are in the electrically open-circuit state.

Thus, it is possible to efficiently prevent the inflow of signals from the outside of the imaging FOV by changing the guard-ring electrode depending on the corresponding FOV.

In the present embodiment, while a direct-detection-type flat panel detector is described, an indirect-type detector may be used as in Embodiment 1.

Embodiment 5

Figure 22:
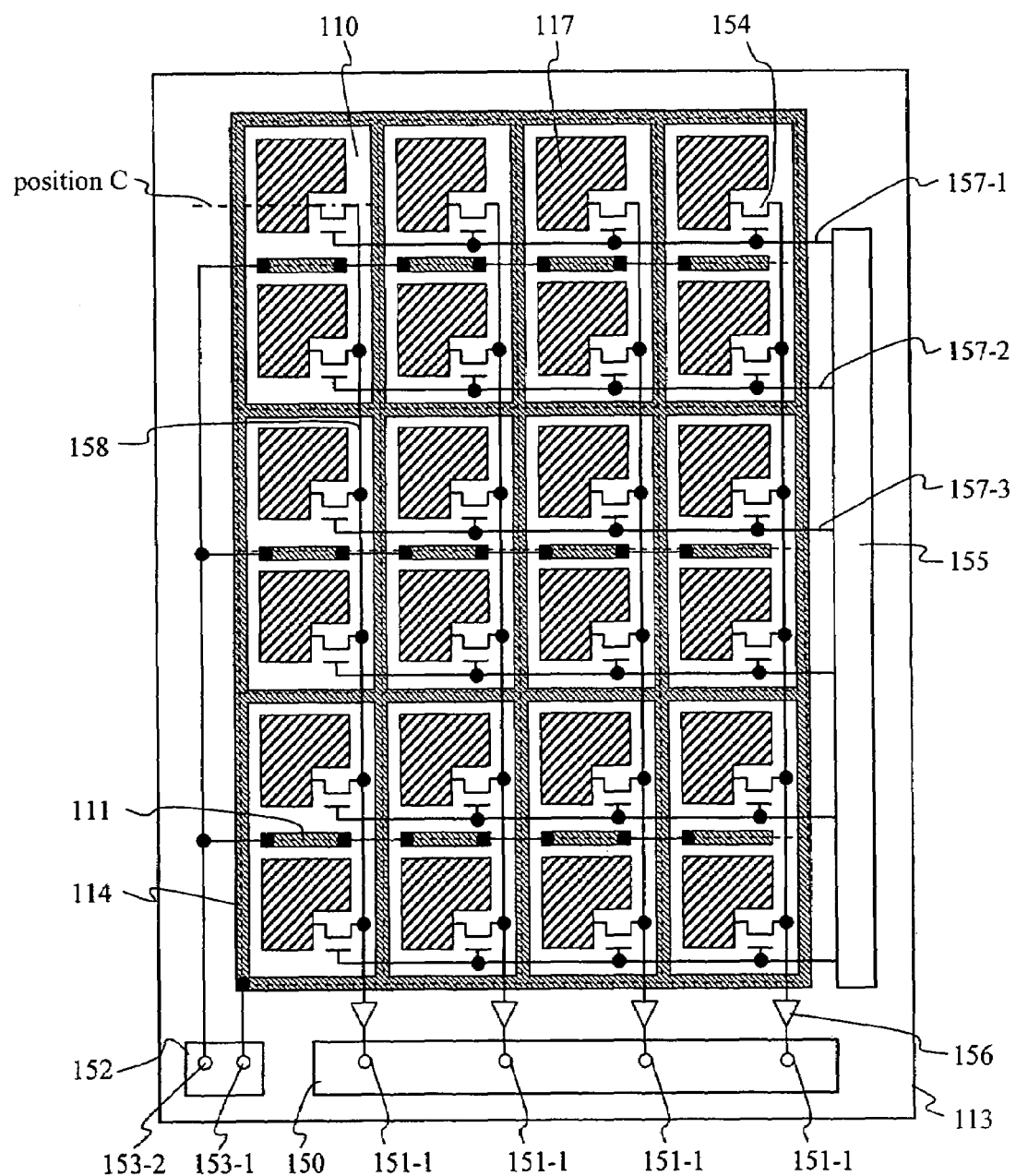
FIG. 22 shows a structural example of X-ray detecting elements and a distribution module.

While an X-ray imaging system of the present embodiment is the same as the X-ray imaging system in Embodiment 4 shown in FIG. 19, the structure and control method of the X-ray detector 104 are different from Embodiment 4; signals are sequentially read and obtained. In order to realize such readout, the X-ray detector 104 of the present embodiment, as one example thereof, comprises the X-ray detecting elements 110 and the distribution module 113, as shown in FIG. 22. As shown in FIG. 22, the X-ray detector 104 of the present embodiment comprises a switch 154 for each of the X-ray detecting elements 110. The drain electrode of each switch 154 is connected to each of the pixel electrodes 117, the source electrode is connected to a terminal 151 of the connector 150 by a common signal line 158 for each column via an integrator 156, and the gate electrode is connected to a shift register 155 by a common control line 157 for each row. Note that the control line in the j-th row is designated by 157-j, and the terminal in the i-th column is designated by 151-i in FIG. 22. Further, while the flat panel detector 104 of the present embodiment is provided with the X-ray detecting elements 110 in a matrix form having six rows and four columns, the number of the X-ray detecting elements 110 is merely an example, and thus the present invention is not limited thereto.

The pixel electrodes 117 are disposed at certain intervals in the X direction, and they are also disposed at certain intervals in the Y direction. The interelement guard-ring electrodes 111 or the peripheral guard-ring electrodes are disposed among their adjacent pixel electrodes 117. The width of each of the interelement guard-ring electrodes 111 and the width of each of the peripheral guard-ring electrodes are less than the width of each of the pixel electrodes 117.

Figure 24:
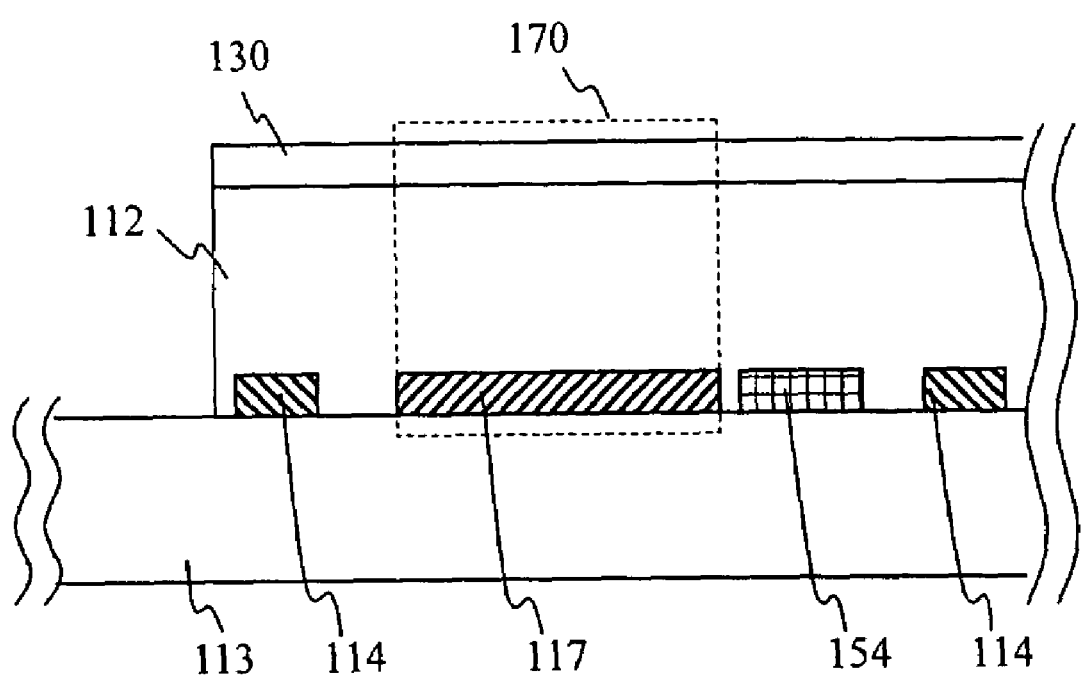
FIG. 24 shows a cross-sectional structure of an X-ray detector.

A method for reading X-ray detection signals based on this X-ray detector 104 will be described. When X rays become incident, they are detected by the photoelectric conversion layer 112, and electrons and holes are then generated. FIG. 24 shows a cross-sectional view of the X-ray detector 104 taken along position C in FIG. 22. As shown in the figure, since the electrode 117 and the common electrode 130 are paired and has a capacitor structure having capacitance at least in a region 170, these electrical charges are accumulated in the capacitor. For example, when the electric potential of the common electrode 130 is greater than that of the electrode 117, the electrons are drawn to the common electrode 130 and the holes are drawn to the electrode 117, whereby they are individually accumulated. In order to read these electrical charges, first, the shift register 155 inputs a signal (to be hereafter referred to as an "on-signal") for turning on the switch 154 only to a control line 157-1, and the electrical charges of all the X-ray detecting elements 110 in the first row are read. The electrical charges are read for each column, and they are then integrated by the integrators 156. Thus, voltage signals are generated, and the signals are individually outputted from the terminals 151. Next, when on-signals are sequentially inputted to the control lines 157-2, 157-3, and so on, the output from the X-ray detecting elements 110 in different rows can be obtained from the same terminal 151. During such readout, by connecting terminals 153-1 and 153-2 to ground potential and applying ground potential to the peripheral guard-ring electrodes 114 and interelement guard-ring electrodes 111, it becomes possible to guard-ring the inflow of signals from the adjacent X-ray detecting elements 110.

The X-ray detector 104 of the present embodiment has a function of conducing binning on the output from two X-ray detecting elements 110 in the row direction. This is achieved by exerting control such that the binning is not conducted in the case of the radiography and the binning is conducted in the case of the fluoroscopy, for example.

When conducting the binning, the shift register 155 simultaneously inputs on-signals to the control lines 157-1 and 157-2. In such case, while the terminal 153-1 is connected to ground potential, the terminal 153-2 is not connected to ground potential; that is, the terminal 153-2 is caused to be in the electrically open-circuit state, so as to apply a voltage only to the peripheral guard-ring electrode 114. In this way, the signals from the X-ray detecting elements 110 in the first row and the second row in the same column are added and then outputted, and X-ray signals incident in the space therebetween are also read from these X-ray detecting elements 110. Further, due to the peripheral guard-ring electrode 114, the two X-ray detecting elements 110 can guard-ring the inflow of signals from the outside thereof. Next, on-signals are simultaneously inputted to the control lines 157-3 and 157-4, and in this way, similarly, it becomes possible to obtain the output from the X-ray detecting elements 110 in the third row and the fourth row on which binning has been conducted. By sequentially conducting such binning, projection images can be obtained.

Based on such structure and control of the X-ray detector 104, when the binning is not conducted, the cross-talk between the X-ray detecting elements 110 is sufficiently suppressed, and when the binning is conducted, the inflow of signals from the outside of the X-ray detecting elements 110 on which the binning is conducted can be suppressed, and X-ray signals inputted into the space between these X-ray detecting elements 110 can be detected and used. Thus, improvement in image quality can be realized due to reduction in unnecessary radiation exposure or increase in the amount of signal.

Further, the present embodiment can be carried out together with the change of the guard-ring electrodes depending on the imaging FOV described in Embodiment 4.

While the electrons generated by radiation are accumulated in the capacitor formed by each of the electrodes 117 and the common electrode 130 in the present embodiment, this is merely an example; the present invention is not limited thereto. A capacitor may be formed separately, so as to accumulate electrical charges in the capacitor.

While the pixel electrodes 117 are disposed at certain intervals in the X direction and the Y direction and the width thereof is also constant in the present embodiment, the present invention is not limited thereto. For example, they may be disposed at irregular intervals with respect to the interelement guard-ring electrodes 111 and the width of each of the pixel electrodes 117 between the interelement guard-ring electrodes 111 may be different from each other. In such case, while the guard-ring electrodes 111 are adjacent to the pixel electrodes 117 having different widths, it is desirable that the width of the guard-ring electrodes 111 be less than, particularly, sufficiently less than, the width of the smaller pixel electrode 117. Furthermore, the present invention includes cases in which the pixel electrodes 117 are disposed at irregular intervals in the X direction and/or the Y direction and cases in which the width of each of the pixel electrodes 117 varies in the X direction and/or the Y direction, depending on the location thereof.

Embodiment 6

Figure 23:
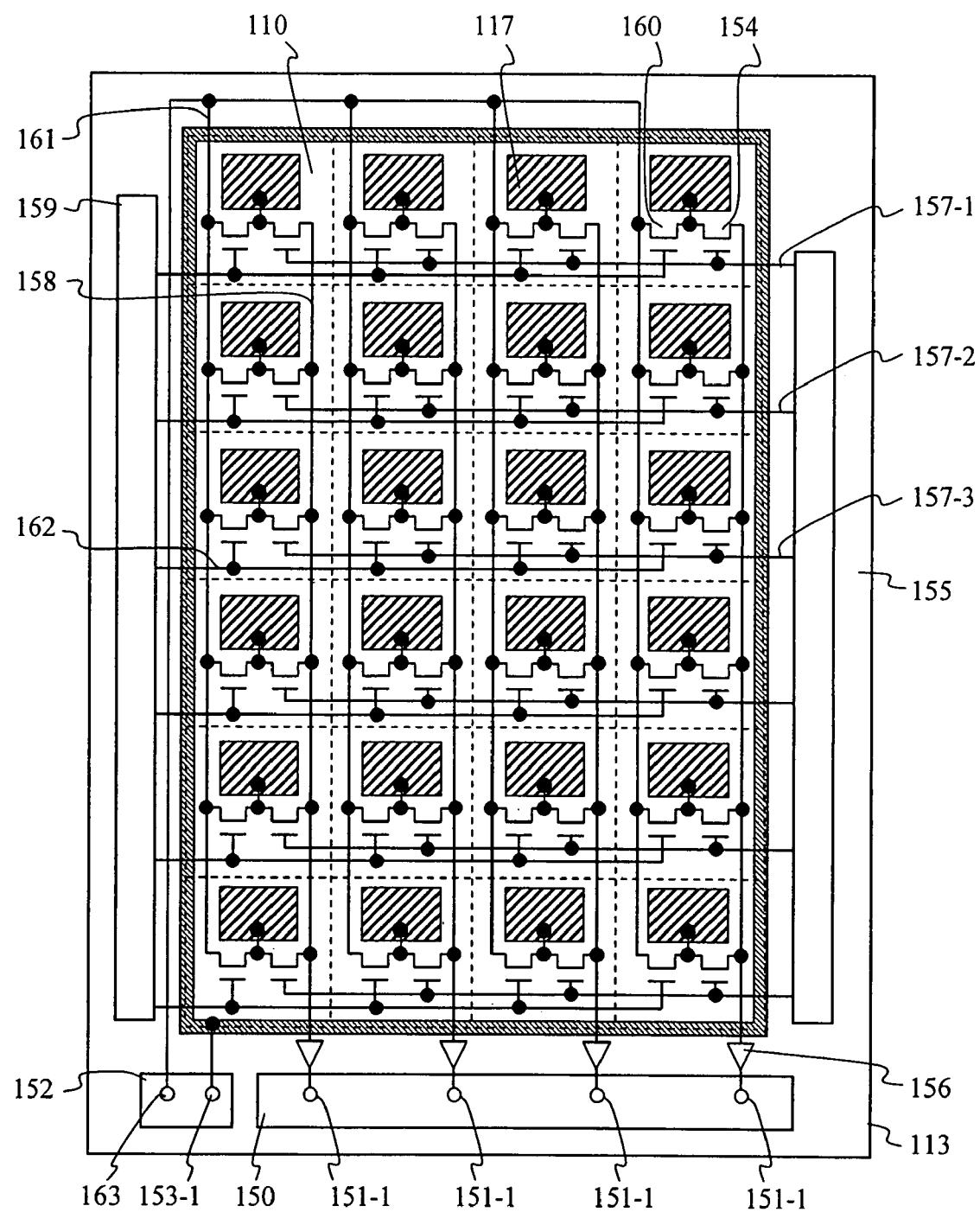
FIG. 23 shows a structural example of X-ray detecting elements and a distribution module.

An X-ray imaging system of the present embodiment is the same as Embodiment 4 shown in FIG. 19 but differs in the structure of the X-ray detector 104. As one example, the X-ray detector 104 of the present embodiment comprises the X-ray detecting elements 110 and the distribution module 113 as shown in FIG. 23. As in the X-ray detector 104 of Embodiment 5, the X-ray detector 104 comprises a switch 154 for each of the X-ray detecting elements 110, a capacitor is formed by each of the electrodes 117 and the common electrode 130, X rays are detected by the photoelectric conversion layer 112, electrical charges thus generated are accumulated in the capacitor, and the switch 154 is controlled by the shift register 155 as in Embodiment 5. Thus, it becomes possible to sequentially obtain the output from the X-ray detecting elements 110 in different rows from the terminal 151 for each column. Further, the X-ray detecting elements 110 of the X-ray detector 104 of the present embodiment comprise switches 160. When these switches 160 are switched for each column by a switch controller 159 electrically connected to a control line 162 and an on-voltage is then inputted, a voltage applied to a terminal 163 electrically connected to a signal line 161 is applied to the corresponding electrode 117.

The X-ray imaging system of the present embodiment has a function of changing the number of rows that perform readout depending on the imaging FOV. For example, while signals are obtained from the FOV including all the rows and columns of FIG. 23 in the case of a wide-field imaging, signals only from the central third and fourth rows are obtained in the case of a narrow-field imaging.

In the case of the wide-field imaging, the controller 115 shown in FIG. 19 controls the collimator 109 so as to limit the irradiation field to the imaging FOV, causes the X-ray tube 100 to emit X rays, connects the terminal 153-1 to ground potential so as to conduct guard-ring, and reads signals from the X-ray detecting elements 110 within the imaging FOV. On the other hand, in the case of the narrow-field imaging, in a state in which the terminal 163 is connected to ground potential, on-signals are outputted through the switch controller 159 to the switches 160 in the second and fifth rows. Thereby, a voltage of ground potential can be applied to the electrodes 117 in the second and fifth rows, and a guard-ring electrode that guard-rings the inflow of cross-talk signals from the outside of the imaging FOV can be realized. Based on such structure and control of the X-ray detector 104, when the imaging FOV is changed, the electrodes of the X-ray detecting elements 110 can be used as guard-ring electrodes according to need. Namely, the electrodes 117 can function as pixel electrodes when connected to a circuit for reading signals used for imaging via a connecting means or the like at the time of imaging and they can function as guard-ring electrodes when they are not connected to the circuit. In this way, by controlling the connection of the electrodes 117 to the readout circuit, it is possible to control the range of the imaging FOV.

The number of X-ray detecting elements 110 of the flat panel detector 104 shown in the present embodiment, the number of the imaging FOV, the range of the imaging FOV, or the like is merely an example. The present invention is not limited thereto.

While the structure in which the guard ring can be changed only in the row direction is described in the present embodiment, the present invention is not limited thereto. The present invention includes cases in which the switches 160 are commonly connected to the switch controller 159 in the column direction so that the switches 160 are controlled in accordance with the imaging FOV and cases in which each of the switches 160 is connected to the switch controller 159 for each of the X-ray detecting elements 110 so that each of the switches 160 is controlled. Further, the present invention includes various variations, including cases in which all of the X-ray detecting elements 110 are not provided with the switches 160 but only the X-ray detecting elements 110 disposed around the narrow-field imaging region are provided with the switches 160, which are connected to the switch controller 159 and controlled in accordance with the imaging FOV, for example.

While embodiments of a medical X-ray CT scanner will be described in the above Embodiments 1 to 3, the present invention is not limited thereto. Needless to say, the present invention can be applied to a variety of apparatus, such as an apparatus equipped with the X-ray detector 104 described in the embodiments or an apparatus equipped with the controller 115, the data acquisition system 118, the central processor 105, and the like. Examples of such apparatus include CT scanners for nondestructive testing, X-ray cone-beam CT, and dual energy CT. Further, while embodiments of an X-ray digital radiography system are described in the above Embodiments 4 to 6, the present invention is not limited thereto. Needless to say, the present invention can be applied to a variety of apparatus, such as an apparatus equipped with the X-ray detector 104 described in the embodiments or an apparatus equipped with the controller 115, the data acquisition system 118, the central processor 105, and the like. Examples of such apparatus include general-purpose X-ray systems, radiation microscopes that conduct imaging using radiation detectors, radiation/X-ray imaging systems for gamma cameras, and radiation/X-ray imaging systems for space, astronomic, or environmental observation and for the imaging thereof. The present invention can be applied to a variety of apparatus, irrespective of business, research, or educational purposes.

Furthermore, the present invention is not limited to the above embodiments; the present invention can be carried out in various ways without departing from the gist of the invention. Further, the above embodiments include various stages, and various variations can be extracted by suitably combining a plurality of disclosed constituent features. For example, some of the constituent features shown in the embodiments may be deleted.

What is claimed is:

1. A radiation detector, comprising:
   a photoelectric conversion layer;
   a plurality of pixel electrodes with which the photoelectric conversion layer is provided;
   a common electrode with which the photoelectric conversion layer is provided so that the common electrode is opposite to the plurality of pixel electrodes;
   a guard-ring electrode disposed between adjacent pixel electrodes that comprise at least part of the plurality of pixel electrodes; and
   a controller for switching a terminal connected to the guard-ring electrode between an electrically open-circuit state and a ground-potential connection state,
   wherein the controller controls the area of a radiation detecting region based on the switching between the electrically open-circuit state and the ground-potential connection state.

2. The radiation detector according to claim 1, comprising:
   a peripheral guard-ring electrode provided so that it surrounds the plurality of pixel electrodes; and
   means for connecting the peripheral guard-ring electrode to ground potential.

3. The radiation detector according to claim 1, wherein, when one region of the plurality of pixel electrodes is used as a radiation detecting region, the controller connects the guard-ring electrode that is located outside the radiation detecting region and that is adjacent to pixel electrodes in the radiation detecting region to the ground potential.

4. The radiation detector according to claim 1, comprising a binning means for conducting binning on adjacent pixel electrodes sandwiching the guard-ring electrode, wherein, when the binning means conducts the binning, the controller causes the terminal of the guard-ring electrode sandwiched between the pixel electrodes on which the binning is conducted to be in the open-circuit state.

5. The radiation detector according to claim 4, wherein, when the binning means conducts the binning, the controller adds an output signal from the pixel electrodes on which the binning is conducted and an output signal from the guard-ring electrode sandwiched between the pixel electrodes on which the binning is conducted, and the controller then outputs the signal added.

6. The radiation detector according to claim 1, comprising:
a capacitor for accumulating electrical charges generated in the photoelectric conversion layer by radiation irradiation;
a plurality of switches, each of which is provided in each of the pixel electrodes, for switching the output of electrical charges accumulated in each of the pixel electrodes; and
a readout circuit for controlling the switches and sequentially reading the electrical charges accumulated in each of the plurality of pixel electrodes.

7. The radiation detector according to claim 1, wherein the width of the guard-ring electrode is less than the width of each of the pixel electrodes that sandwich the guard-ring electrode in the direction in which the plurality of pixel electrodes sandwich the guard-ring electrode.

8. An X-ray imaging system, comprising:
an X-ray tube for generating X rays;
a radiation detector that is disposed opposite to the X-ray tube and that comprises a photoelectric conversion layer, a plurality of pixel electrodes with which the photoelectric conversion layer is provided, a common electrode with which the photoelectric conversion layer is provided so that the common electrode is opposite to the plurality of pixel electrodes, and a guard-ring electrode that is disposed between adjacent pixel electrodes that comprise at least part of the plurality of pixel electrodes;
a controller for switching a terminal connected to the guard-ring electrode between an electrically open-circuit state and a ground-potential connection state;
signal processing means for conducting a signal processing with respect to signals from the radiation detector;
an image display unit for displaying the results of the signal processing; and
imaging field changing means for changing an imaging field of view,
wherein the controller, depending on the change in field of view conducted by the imaging field changing means, connects the guard-ring electrode that is located outside a radiation detecting region and that is adjacent to pixel electrodes in the radiation detecting region to the ground potential.

9. The X-ray imaging system according to claim 8, wherein the radiation detector comprises a peripheral guard-ring electrode provided so that it surrounds the plurality of pixel electrodes, and the controller connects the peripheral guard-ring electrode to ground potential.

10. The X-ray imaging system according to claim 8, comprising:
a capacitor for accumulating electrical charges generated in the photoelectric conversion layer by X-ray irradiation;
a plurality of switches, each of which is provided in each of the pixel electrodes, for switching the output of electrical charges accumulated in each of the pixel electrodes; and
a readout circuit for controlling the switches and sequentially reading the electrical charges accumulated in each of the plurality of pixel electrodes.

11. An X-ray imaging system, comprising:
an X-ray tube for generating X rays;
a radiation detector that is disposed opposite to the X-ray tube and that comprises a photoelectric conversion layer, a plurality of pixel electrodes with which the photoelectric conversion layer is provided, a common electrode with which the photoelectric conversion layer is provided so that the common electrode is opposite to the plurality of pixel electrodes, and a guard-ring electrode that is disposed between adjacent pixel electrodes that comprise at least part of the plurality of pixel electrodes;
a controller for switching a terminal connected to the guard-ring electrode between an electrically open-circuit state and a ground-potential connection state;
signal processing means for conducting a signal processing with respect to signals from the radiation detector;
an image display unit for displaying the results of the signal processing; and
binning means for conducting binning on the adjacent pixel electrode,
wherein, when the binning means is used, the controller causes the terminal of the guard-ring electrode sandwiched between the pixel electrodes on which the binning is conducted to be in the open-circuit state.

12. The X-ray imaging system according to claim 11, wherein, when the binning means is used, the controller adds an output signal from the pixel electrode on which the binning is conducted and an output signal from the guard-ring electrode sandwiched between the pixel electrodes on which the binning is conducted, and the controller then outputs the signal added.

13. The X-ray imaging system according to claim 11, wherein the width of the guard-ring electrode is less than the width of each of the pixel electrodes that sandwich the guard-ring electrode in the direction in which the plurality of pixel electrodes sandwich the guard-ring electrode.

14. The X-ray imaging system according to claim 11, comprising:
a capacitor for accumulating electrical charges generated in the photoelectric conversion layer by X-ray irradiation;
a plurality of switches, each of which is provided in each of the pixel electrodes, for switching the output of electrical charges accumulated in each of the pixel electrodes; and
a readout circuit for controlling the switches and sequentially reading the electrical charges accumulated in each of the plurality of pixel electrodes.

15. An X-ray CT scanner, comprising:
an X-ray tube for generating X rays;
an X-ray detector comprising a plurality of radiation detectors disposed opposite to the X-ray tube in an arc, each of the radiation detectors comprising a photoelectric conversion layer, a plurality of pixel electrodes provided on one surface of the photoelectric conversion layer, a common electrode provided on the other surface of the photoelectric conversion layer so that the common electrode is opposite to the plurality of pixel electrodes, and a guard-ring electrode that is disposed between adjacent pixel electrodes that comprise at least part of the plurality of pixel electrodes, and each of the radiation detectors having a structure in which the pixel electrodes are two-dimensionally disposed in the channel direction and the slice direction;

a controller for switching a terminal connected to the guard-ring electrode of the radiation detector between an electrically open-circuit state and a ground-potential connection state;

arithmetic processing means for conducting a signal processing and a reconstruction processing based on signals from the radiation detector;

an image display unit for displaying the results of the arithmetic processing means; and imaging field changing means for changing the size of an imaging field of view in the slice direction, wherein the controller, depending on the change in the size of field of view conducted by the imaging field changing means, connects the guard-ring electrode that is located outside a radiation detecting region and that is adjacent to pixel electrodes in the radiation detecting region to the ground potential.

16. The X-ray CT scanner according to claim 15, wherein the radiation detector comprises a peripheral guard-ring electrode provided so that it surrounds the plurality of pixel electrodes, and the controller connects the peripheral guard-ring electrode to ground potential.

17. An X-ray CT scanner, comprising:

an X-ray tube for generating X rays;

an X-ray detector comprising a plurality of radiation detectors disposed opposite to the X-ray tube in an arc, each of the radiation detectors comprising a photoelectric conversion layer, a plurality of pixel electrodes provided on one surface of the photoelectric conversion layer, a common electrode provided on the other surface of the photoelectric conversion layer so that the common electrode is opposite to the plurality of pixel electrodes, and a guard-ring electrode that is disposed between adjacent pixel electrodes that comprise at least part of the plurality of pixel electrodes, and each of the radiation detectors having a structure in which the pixel electrodes are two-dimensionally disposed in the channel direction and the slice direction;

a controller for switching a terminal connected to the guard-ring electrode of the radiation detector between an electrically open-circuit state and a ground-potential connection state;

arithmetic processing means for conducting a signal processing and a reconstruction processing based on signals from the radiation detector;

an image display unit for displaying the results of the arithmetic processing means; and binning means for conducting binning on the adjacent pixel electrodes, wherein, when the binning means is used, the controller causes the terminal of the guard-ring electrode sandwiched between the pixel electrodes on which the binning is conducted to be in the open-circuit state.

18. The X-ray CT scanner according to claim 17, wherein, when the binning means is used, the controller adds an output signal from the pixel electrodes on which the binning is conducted and an output signal from the guard-ring electrode sandwiched between the pixel electrodes on which the binning is conducted, and the controller then outputs the signal added.

19. The X-ray CT scanner according to claim 17, wherein the width of the guard-ring electrode is less than the width of each of the pixel electrodes that sandwich the guard-ring electrode in the direction in which the plurality of pixel electrodes sandwich the guard-ring electrode.

20. A radiation detector, comprising:

a photoelectric conversion layer;

a plurality of pixel electrodes with which the photoelectric conversion layer is provided;

a common electrode with which the photoelectric conversion layer is provided so that the common electrode is opposite to the plurality of pixel electrodes;

a readout circuit for reading detection signals; and a controller for controlling the connection of the pixel electrodes to the readout circuit, wherein the controller controls the area of a radiation detecting region by controlling the connection to the readout circuit.

* * * * *